(12) United States Patent
Perryman et al.

(10) Patent No.: US 9,907,950 B1
(45) Date of Patent: Mar. 6, 2018

(54) SYSTEM AND METHOD FOR STIMULATION WITH ELECTRODE

(71) Applicant: Micron Devices LLC, Miami Beach, FL (US)

(72) Inventors: Laura Tyler Perryman, Miami Beach, FL (US); Patrick Larson, Surfside, FL (US); Chad Andresen, Miami Beach, FL (US)

(73) Assignee: Micron Devices LLC, Pompano Beach, FL (US)

( * ) Notice: Subject to any disclaimer, the term of this patent is extended or adjusted under 35 U.S.C. 154(b) by 301 days.

(21) Appl. No.: 14/312,234

(22) Filed: Jun. 23, 2014

Related U.S. Application Data

(60) Provisional application No. 61/838,239, filed on Jun. 22, 2013.

(51) Int. Cl.
| | |
|---|---|
| *A61N 1/05* | (2006.01) |
| *A61N 1/372* | (2006.01) |
| *A61N 1/378* | (2006.01) |
| *A61N 1/375* | (2006.01) |
| *A61N 1/36* | (2006.01) |

(52) U.S. Cl.
CPC ....... *A61N 1/0556* (2013.01); *A61N 1/36125* (2013.01); *A61N 1/3756* (2013.01); *A61N 1/3787* (2013.01); *A61N 1/37211* (2013.01)

(58) Field of Classification Search
CPC ............................ A61N 1/0556; A61N 1/0558
USPC ............................................ 607/60, 129, 118
See application file for complete search history.

(56) References Cited

U.S. PATENT DOCUMENTS 5,358,514 A * 10/1994 Schulman .............. A61N 1/372
607/118

* cited by examiner

*Primary Examiner* — Alyssa M Alter
(74) *Attorney, Agent, or Firm* — Fish & Richardson P.C.

(57) ABSTRACT

Some implementations provide a method for modulating excitable tissue in a body of a patient, the method including: placing a wireless implantable stimulator device at a target site in the patient's body, the stimulator device including one or more electrodes; reconfiguring the wireless implantable stimulator device to form an enclosure that substantially surrounds the excitable tissue at the target site with the electrodes on the inside of the enclosure and facing the nerve; and causing electrical impulses to be delivered to the electrodes on the wireless implantable stimulator device such that neural modulation is applied to the excitable tissue substantially surrounded by the enclosure.

25 Claims, 25 Drawing Sheets

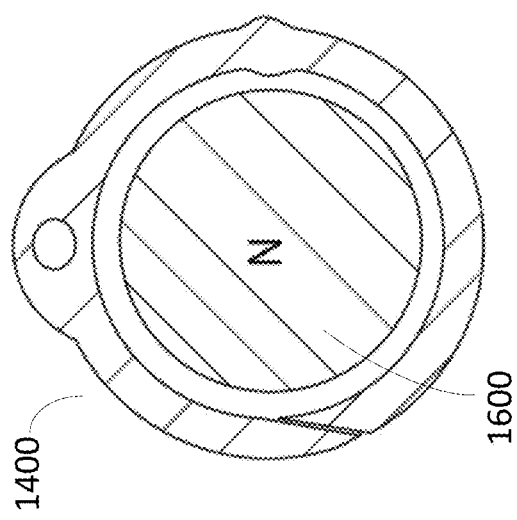

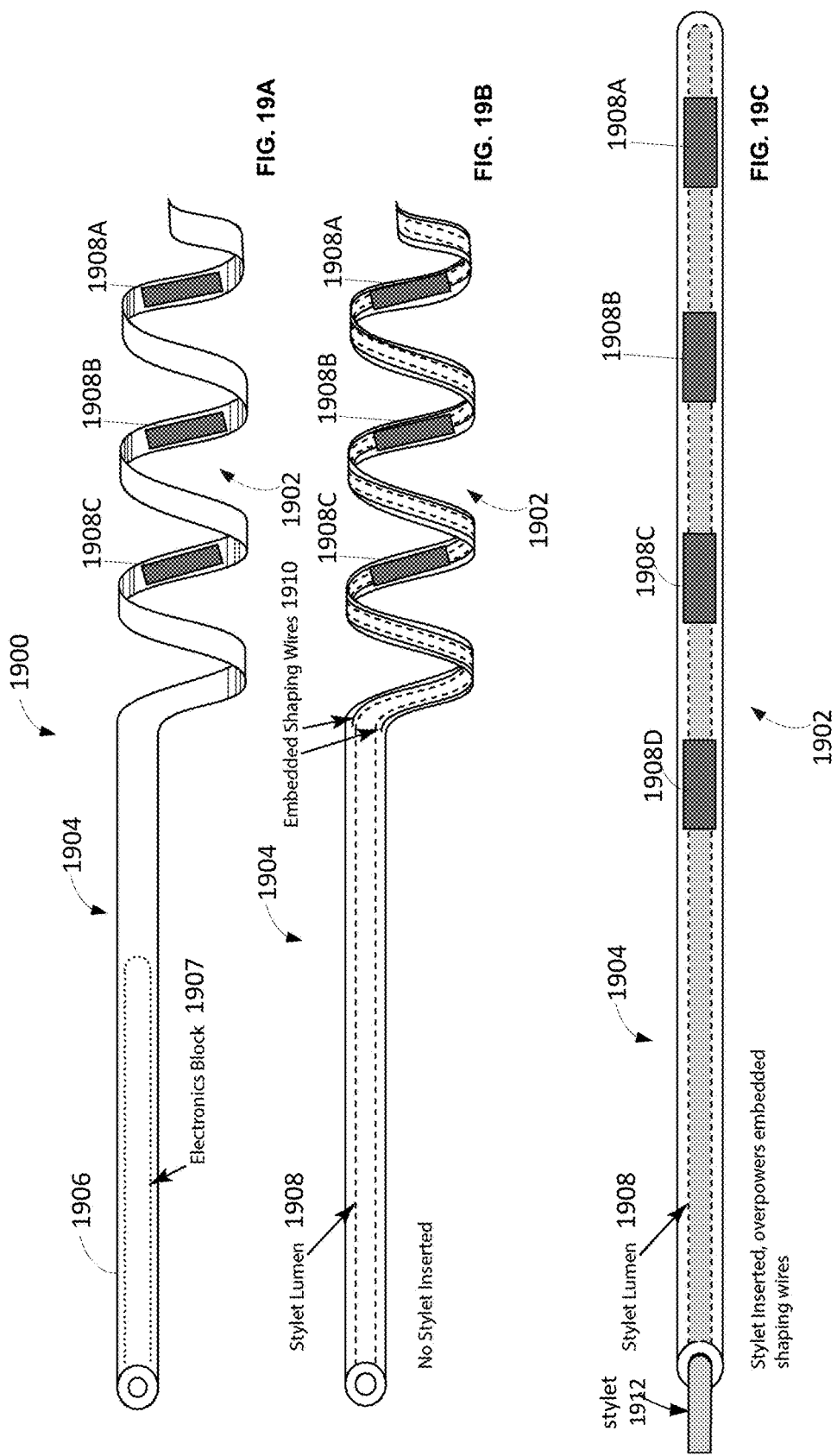

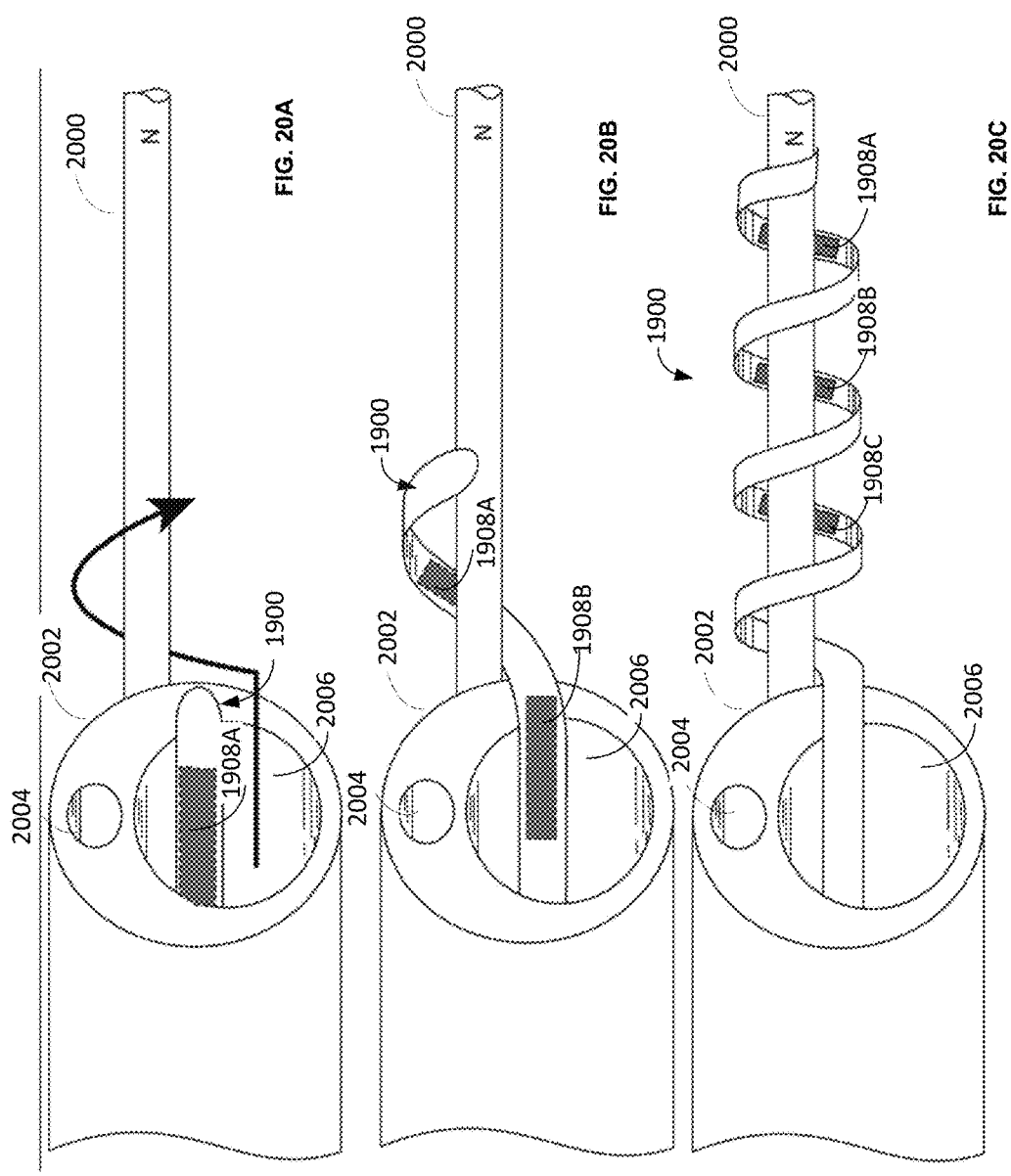

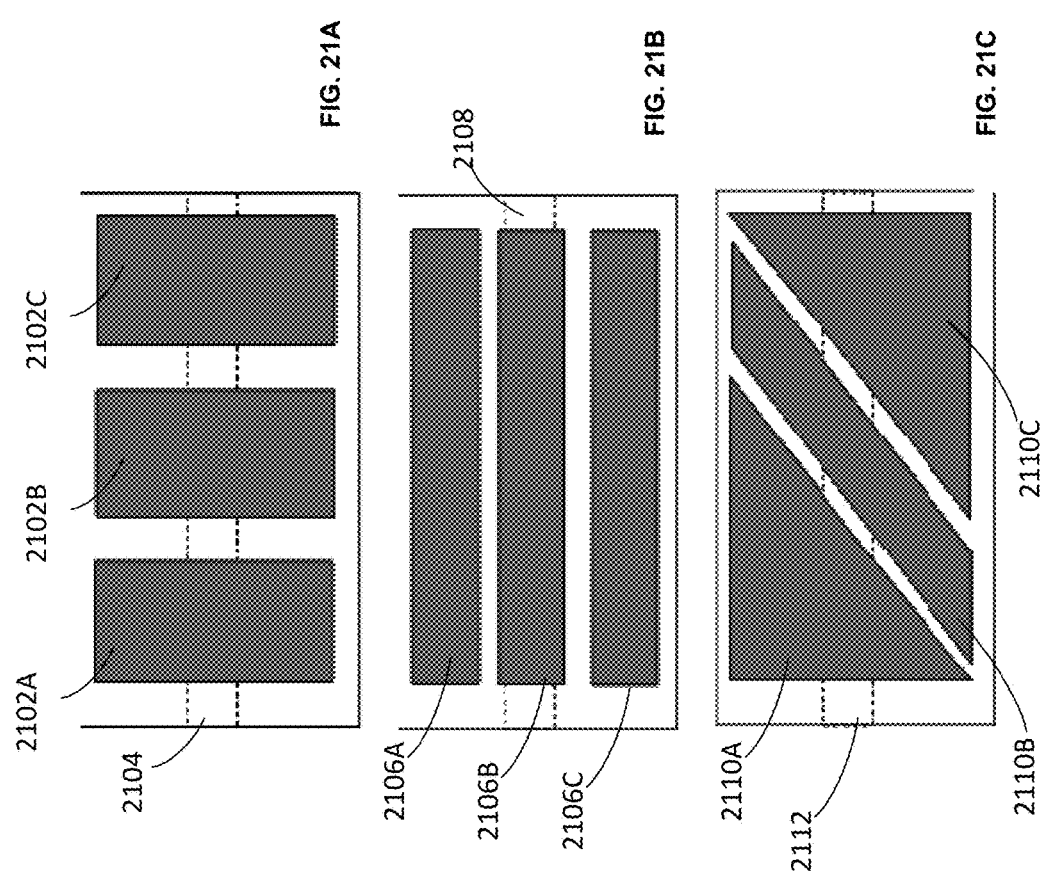

SYSTEM AND METHOD FOR STIMULATION WITH ELECTRODE

CROSS REFERENCE TO RELATED APPLICATIONS

This application claims benefit of U.S. provisional Patent Application 61/838,239, filed Jun. 22, 2013.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

SUMMARY

In one aspect, some implementations provide a method for modulating excitable tissue in a body of a patient, the method including: placing a wireless implantable stimulator device at a target site in the patient's body, the stimulator device including one or more electrodes; reconfiguring the wireless implantable stimulator device to form an enclosure that substantially surrounds the excitable tissue at the target site with the electrodes on the inside of the enclosure and facing the nerve; and causing electrical impulses to be delivered to the electrodes on the wireless implantable stimulator device such that neural modulation is applied to the excitable tissue substantially surrounded by the enclosure.

Implementations may include one or more of the following features. Placing the wireless implantable stimulator device may include: placing an introducer into the patient's body near the target site; constraining a helical wireless implantable stimulator device into a substantially linear shape within an inner lumen of the introducer; and advancing the helical wireless implantable stimulator device through the inner lumen of the introducer to the target site and out of a distal end of the inner lumen of the introducer towards the excitable tissue such that the helical wireless implantable stimulator device spirals around the excitable tissue to form the enclosure substantially surrounding the excitable tissue. The inner lumen of the introducer may be 1.2 mm or less in diameter. Constraining may further include: inserting a stylet into a proximal end of the helical wireless implantable.

Placing the wireless implantable stimulator device may include: surgically creating an opening on the patient's body; through the opening, exposing the excitable tissue at a target site in the patient's body; positioning an unfolded cylindrical implantable stimulator device adjacent to the exposed excitable tissue at the target site; and folding the foldable cylindrical implantable stimulator device around the excitable tissue to form the enclosure substantially surrounding the excitable tissue.

Placing the wireless implantable stimulator device may include: placing an introducer into the patient's body towards the target site; and advancing a foldable cylindrical wireless implantable stimulator device through an inner lumen of the introducer towards the target site until the foldable cylindrical wireless implantable stimulator device exits a distal end of the inner lumen of the introducer in an folded position; unfolding the foldable cylindrical implantable stimulator device; positioning the unfolded cylindrical implantable stimulator device adjacent to the excitable tissue at the target site; and folding the foldable cylindrical implantable stimulator device around the excitable tissue to form the enclosure substantially surrounding the excitable tissue. Unfolding may include: pivoting a portion of the foldable cylindrical wireless stimulator device about a hinge. Folding may include pivoting a portion of the foldable cylindrical wireless stimulator device about a hinge.

The electrodes include directional electrodes. The method may further include: causing electrical energy and waveform parameters to be transmitted from a pulse generator located outside of the patient's body to the wireless implantable stimulator device through electrical radiative coupling such that one or more electrical impulses are applied through the electrodes on the wireless implantable stimulator device, the electrical impulses created from the electrical energy and being sufficient to modulate the nerve.

Some implementations may provide a device for modulating excitable tissue in a patient's body, the device including: a wireless implantable stimulator device that includes one or more electrodes on an inner surface of the wireless implantable stimulator device, wherein the wireless implantable stimulator device is reconfigurable inside the patient's body from a first configuration to a second configuration, the second configuration forming an enclosure that substantially surrounds the excitable tissue such that electrical impulses delivered to the electrodes modulate the excitable tissue substantially surrounded by the enclosure.

Implementations may include one or more of the following features. The first configuration may include a portion of the wireless implantable stimulator device shaped substantially linear and the second configuration includes the portion shaped substantially helical. The portion shaped substantially helical may form the enclosure that substantially surrounds the excitable tissue. The wireless implantable stimulator device may include a cylindrical implantable stimulator device and wherein the first configuration is an open position of the cylindrical implantable stimulator device and the second configuration is a closed position of the cylindrical implantable stimulator device. The implantable stimulator device may further include a hinge, a first portion and a second portion; and wherein the first portion and the second portion are coupled together with the hinge and are pivotable about the hinge to move from the open position to the closed position. The electrodes may include directional electrodes. The wireless implantable stimulator device may further include a receiving antenna and circuitry, wherein the receiving antenna is configured to receive an input signal containing electrical energy and waveform parameters through electrical radiative coupling from a transmitter located outside of the patient's body and wherein the circuitry is configured to create one or more electrical impulses by harvesting the electrical energy from the input signal, the electrical impulse sufficient to modulate the excitable tissue substantially surrounded by the enclosure.

Some implementations may provide a system for modulating excitable tissue in a body of a patient, the system including: an wireless implantable stimulator device including one or more electrodes and a receiving antenna, the stimulator device being reconfigurable inside the patient's body from a first configuration to a second configuration, the second configuration forming an enclosure that substantially surrounds the excitable tissue such that electrical impulses delivered to the electrodes modulate the excitable tissue substantially surrounded by the enclosure; and a control device having a transmitter located outside of the patient's body and configured to transmit an input signal containing electrical energy and waveform parameters to the receiving antenna through electrical radiative coupling, wherein the stimulator device is configured to generate one or more electrical impulses by harvesting the electrical energy from the input signal, the electrical impulses sufficient to modulate the excitable tissue.

Implementations may include one or more of the following features. The control device may include a transmitting antenna configured to transmit the input signal through a carrier signal having a frequency between about 800 KHz and 5.8 GHz. The control device may include a pulse generator configured to generate electrical impulses with a frequency of about 10 to 500 Hz. The control device may be configured to transmit the input signal to the targeted site tissue inside the patient's body within 12 cm of skin surface of the patient. The first position may include a portion of the wireless implantable stimulator device shaped substantially linear and the second position includes is the portion shaped substantially helical. The portion shaped substantially helical may form the enclosure that substantially surrounds the excitable tissue. The electrodes may include directional electrodes and may be positioned on the inner surface of the enclosure. The stimulator device may include a cylindrical implantable stimulator device and wherein the first configuration is an open position of the cylindrical implantable stimulator device and the second configuration is a closed position of the cylindrical implantable stimulator device. The stimulator device may further include a hinge, a first portion and a second portion; and wherein the first portion and the second portion are coupled together with the hinge and are pivotable about the hinge to move from the open position to the closed position.

Various implementations may be inherently low in cost compared to existing implantable neural modulation systems, and this may stimulator device to wider adoption of neural modulation therapy for patients in need as well as reduction in overall cost to the healthcare system.

The details of one or more implementations are set forth in the accompanying drawings and the description below. Other features, objects, and advantages will be apparent from the description and drawings, and from the claims.

BRIEF DESCRIPTION OF THE DRAWINGS

FIGS. 16A to 16B show an example of a cylindrical wireless implantable stimulator device forming an enclosure around a nerve.

FIGS. 19A to 19C show an example of a helical wireless implantable stimulator device.

FIGS. 20A to 20C illustrate an example of the placement of a helical wireless implantable stimulator device through an introducer.

FIGS. 21A to 21C illustrate examples of electrode configurations for various configurations of a wireless implantable stimulator device.

DETAILED DESCRIPTION

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy with neither cables nor inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for sending radio frequency or microwave energy from an external source to the implantable stimulator device with neither cables nor inductive coupling to provide power.

In various embodiments, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil. Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

Figure 1:
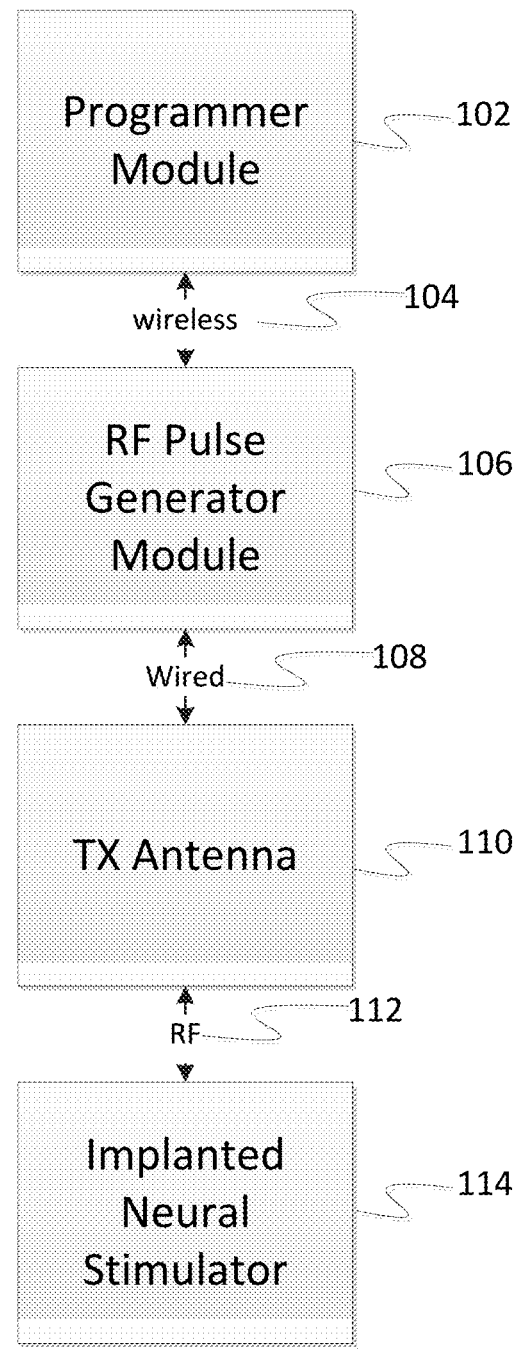
FIG. 1 depicts a high-level diagram of an example of a wireless stimulation system.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112.

In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
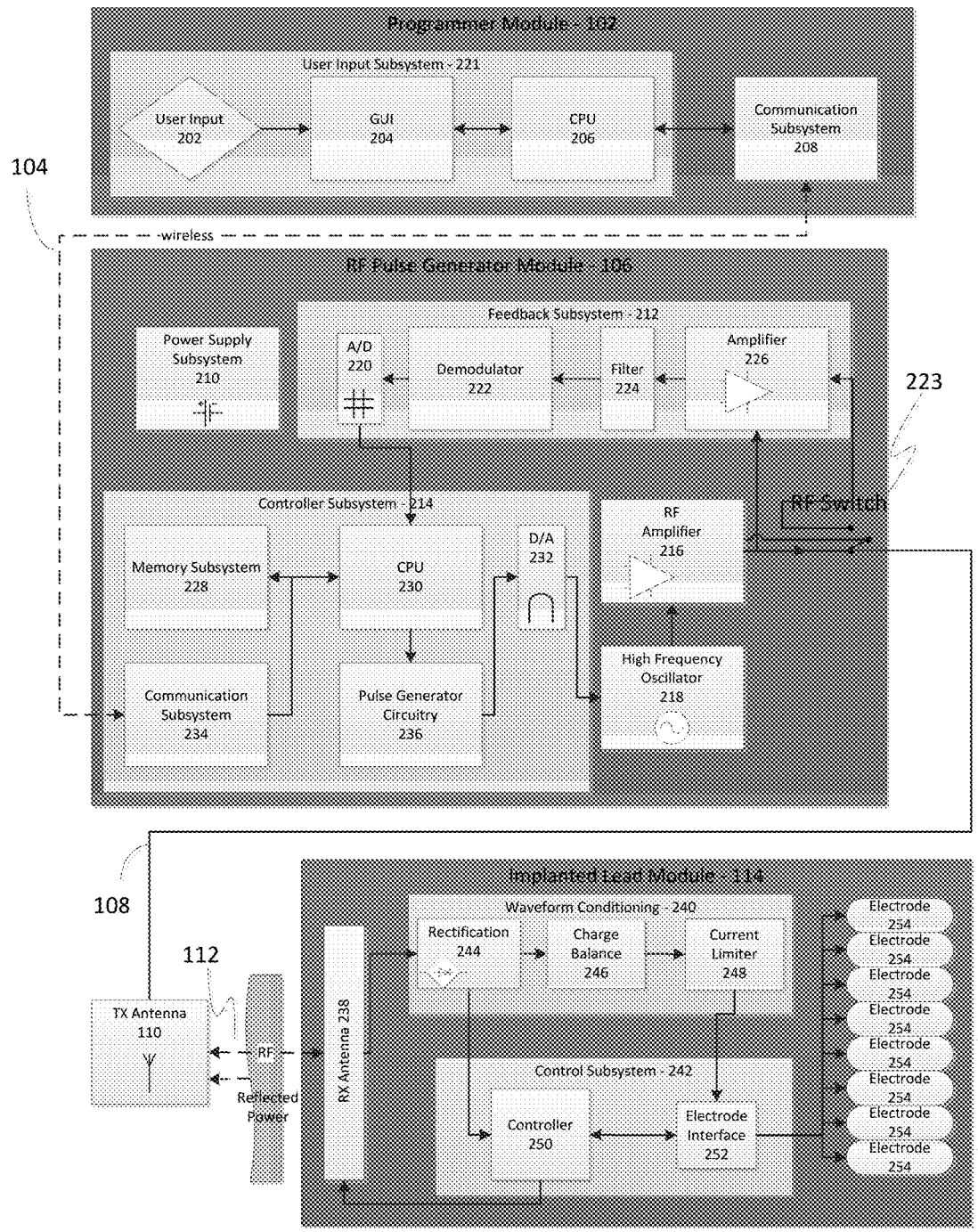
FIG. 2 depicts a detailed diagram of an example of the a wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
|---|---|
| Pulse Amplitude: | 0 to 20 mA |
| Pulse Frequency: | 0 to 10000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receive (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3:
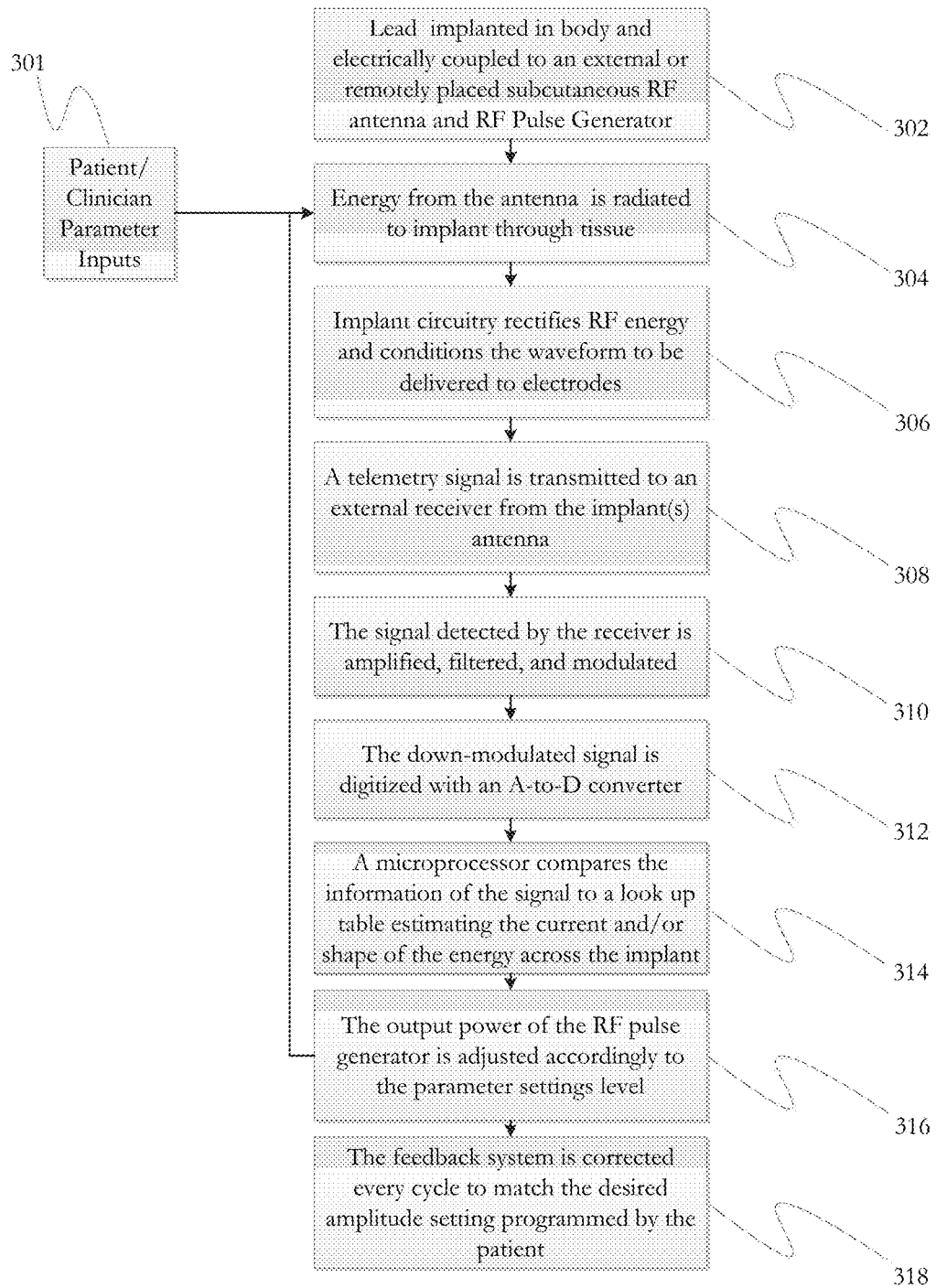
FIG. 3 is a flowchart showing an example of the operation of the wireless stimulation system.

FIG. 3 is a flowchart showing an example of an operation of a wireless neural stimulation system. In block 302, the wireless stimulator device 114 is implanted in proximity to nerve bundles and is coupled to the electric field produced by the TX antenna 110. That is, the pulse generator module 106 and the TX antenna 110 are positioned in such a way (for example, in proximity to the patient) that the TX antenna 110 is electrically radiatively coupled with the implanted RX antenna 238 of the wireless stimulator device 114. In certain implementations, both the antenna 110 and the RF pulse generator 106 are located subcutaneously. In other implementations, the antenna 110 and the RF pulse generator 106 are located external to the patient's body. In this case, the TX antenna 110 may be coupled directly to the patient's skin.

Energy from the RF pulse generator is radiated to the implanted wireless stimulator device 114 from the antenna 110 through tissue, as shown in block 304. The energy radiated may be controlled by the Patient/Clinician Parameter inputs in block 301. In some instances, the parameter settings can be adjusted in an open loop fashion by the patient or clinician, who would adjust the parameter inputs in block 301 to the system.

The implanted wireless stimulator device 114 uses the received energy to generate electrical pulses to be applied to the neural tissue through the electrodes 238. For instance, the wireless stimulator device 114 may contain circuitry that rectifies the received RF energy and conditions the waveform to charge balance the energy delivered to the electrodes to stimulate the targeted nerves or tissues, as shown in block 306. The implanted wireless stimulator device 114 communicates with the pulse generator 106 by using antenna 238 to send a telemetry signal, as shown in block 308. The telemetry signal may contain information about parameters of the electrical pulses applied to the electrodes, such as the impedance of the electrodes, whether the safe current limit has been reached, or the amplitude of the current that is presented to the tissue from the electrodes.

In block 310, the RF pulse generator 106 detects amplifies, filters and modulates the received telemetry signal using amplifier 226, filter 224, and demodulator 222, respectively. The A/D converter 230 then digitizes the resulting analog signal, as shown in 312. The digital telemetry signal is routed to CPU 230, which determines whether the parameters of the signal sent to the wireless stimulator device 114 need to be adjusted based on the digital telemetry signal. For instance, in block 314, the CPU 230 compares the information of the digital signal to a look-up table, which may indicate an appropriate change in stimulation parameters. The indicated change may be, for example, a change in the current level of the pulses applied to the electrodes. As a result, the CPU may change the output power of the signal sent to wireless stimulator device 114 so as to adjust the current applied by the electrodes 254, as shown in block 316.

Thus, for instance, the CPU 230 may adjust parameters of the signal sent to the wireless stimulator device 114 every cycle to match the desired current amplitude setting programmed by the patient, as shown in block 318. The status of the stimulator system may be sampled in real time at a rate of 8 Kbits per second of telemetry data. All feedback data received from the wireless stimulator device 114 can be maintained against time and sampled per minute to be stored for download or upload to a remote monitoring system accessible by the health care professional for trending and statistical correlations in block 318. If operated in an open loop fashion, the stimulator system operation may be reduced to just the functional elements shown in blocks 302, 304, 306, and 308, and the patient uses their judgment to adjust parameter settings rather than the closed looped feedback from the implanted device.

Figure 4:
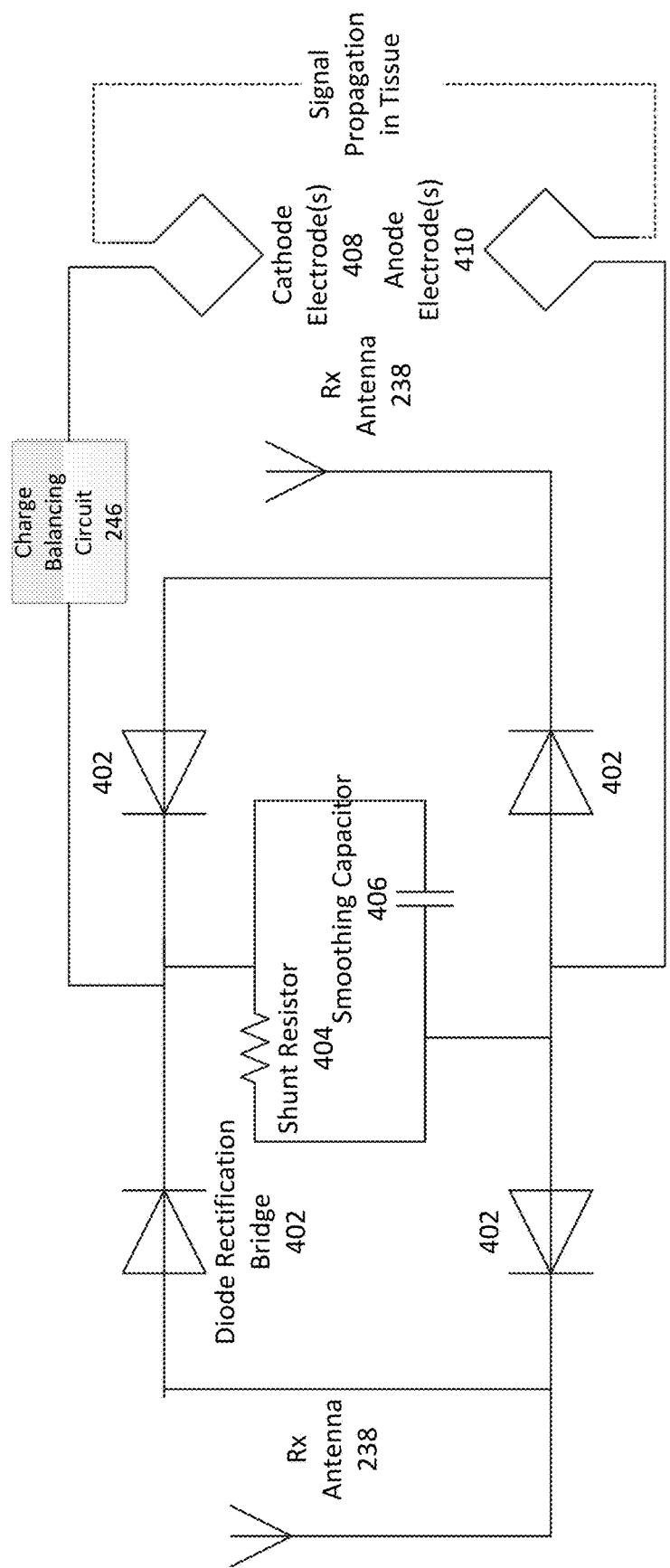
FIG. 4 is a circuit diagram showing an example of a wireless implantable stimulator device.

FIG. 4 is a circuit diagram showing an example of a wireless stimulator device 114. This example contains paired electrodes, comprising cathode electrode(s) 408 and anode electrode(s) 410, as shown. When energized, the charged electrodes create a volume conduction field of current density within the tissue. In this implementation, the wireless energy is received through a dipole antenna(s) 238. At least four diodes are connected together to form a full wave bridge rectifier 402 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 includes two branches of diode pairs connecting an anode-to-anode and then cathode to cathode. The electrodes 408 and 410 are connected to the output of the charge balancing circuit 246.

Figure 5:
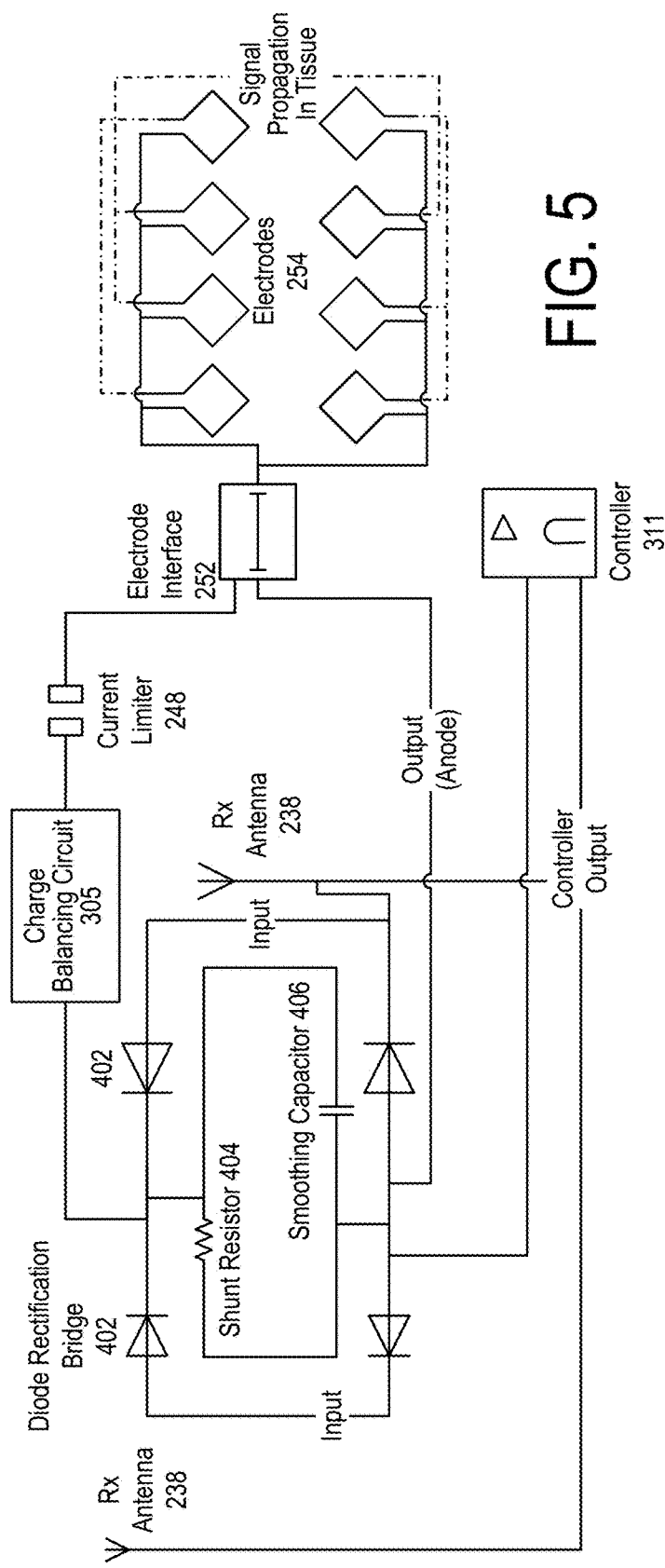
FIG. 5 is a circuit diagram of another example of a wireless implantable stimulator device.

FIG. 5 is a circuit diagram of another example of a wireless stimulator device 114. The example shown in FIG. 5 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 may include two branches of diode pairs connecting an anode-to-anode and then cathode to cathode. The electrode polarity outputs, both cathode 408 and anode 410 are connected to the outputs formed by the bridge connection. Charge balancing circuitry 246 and current limiting circuitry 248 are placed in series with the outputs.

Figure 6:
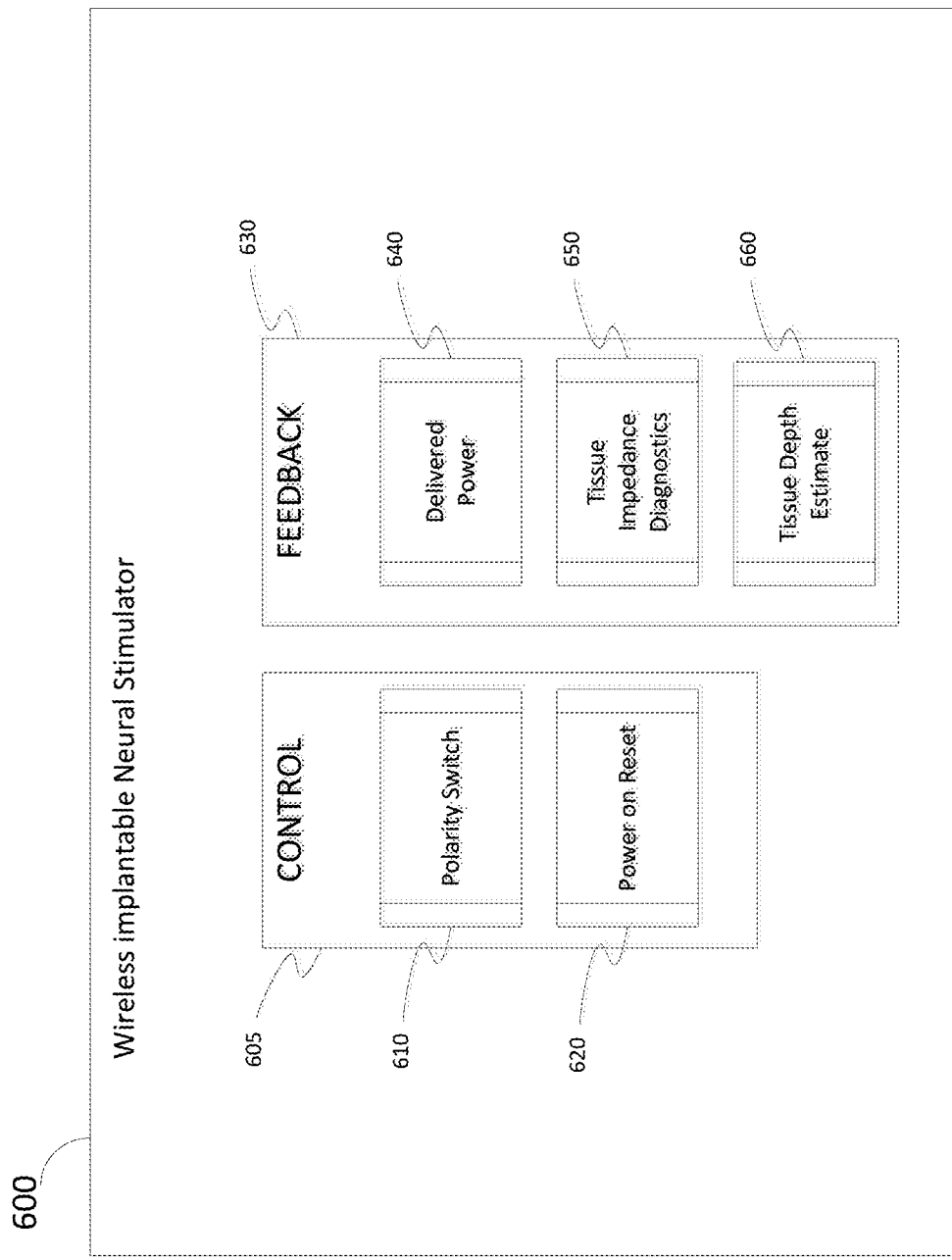
FIG. 6 is a block diagram showing an example of control and feedback functions of a wireless implantable stimulator device.

FIG. 6 is a block diagram showing an example of control functions 605 and feedback functions 630 of an implantable wireless stimulator device 600, such as the ones described above or further below. An example implementation may be a wireless stimulator device module 114, as discussed above in association with FIG. 2. Control functions 605 include functions 610 for polarity switching of the electrodes and functions 620 for power-on reset.

Polarity switching functions 610 may employ, for example, a polarity routing switch network to assign polarities to electrodes 254. The assignment of polarity to an electrode may, for instance, be one of: a cathode (negative polarity), an anode (positive polarity), or a neutral (off) polarity. The polarity assignment information for each of the electrodes 254 may be contained in the input signal received by implantable wireless stimulator device 600 through Rx antenna 238 from RF pulse generator module 106. Because a programmer module 102 may control RF pulse generator module 106, the polarity of electrodes 254 may be controlled remotely by a programmer through programmer module 102, as shown in FIG. 2.

Power-on reset functions 620 may reset the polarity assignment of each electrode immediately on each power-on event. As will be described in further detail below, this reset operation may cause RF pulse generator module 106 to transmit the polarity assignment information to the implantable wireless stimulator device 600. Once the polarity assignment information is received by the implantable wireless stimulator device 600, the polarity assignment information may be stored in a register file, or other short-term memory component. Thereafter the polarity assignment information may be used to configure the polarity assignment of each electrode. If the polarity assignment information transmitted in response to the reset encodes the same polarity state as before the power-on event, then the polarity state of each electrode can be maintained before and after each power-on event.

Feedback functions 630 include functions 640 for monitoring delivered power to electrodes 254 and functions 650 for making impedance diagnosis of electrodes 254. For example, delivered power functions 640 may provide data encoding the amount of power being delivered from electrodes 254 to the excitable tissue and tissue impedance diagnostic functions 650 may provide data encoding the diagnostic information of tissue impedance. The tissue impedance is the electrical impedance of the tissue as seen between negative and positive electrodes when a stimulation current is being released between negative and positive electrodes.

Feedback functions 630 may additionally include tissue depth estimate functions 660 to provide data indicating the overall tissue depth that the input radio frequency (RF) signal from the pulse generator module, such as, for example, RF pulse generator module 106, has penetrated before reaching the implanted antenna, such as, for example, RX antenna 238, within the wireless implantable stimulator device 600, such as, for example, implanted wireless stimulator device 114. For instance, the tissue depth estimate may be provided by comparing the power of the received input signal to the power of the RF pulse transmitted by the RF pulse generator 106. The ratio of the power of the received input signal to the power of the RF pulse transmitted by the RF pulse generator 106 may indicate an attenuation caused by wave propagation through the tissue. For example, the second harmonic described below may be received by the RF pulse generator 106 and used with the power of the input signal sent by the RF pulse generator to determine the tissue depth. The attenuation may be used to infer the overall depth of implantable wireless stimulator device 600 underneath the skin.

The data from blocks 640, 650, and 660 may be transmitted, for example, through Tx antenna 110 to an implantable RF pulse generator 106, as illustrated in FIGS. 1 and 2.

As discussed above in association with FIGS. 1, 2, 4, and 5, a implantable wireless stimulator device 600 may utilize rectification circuitry to convert the input signal (e.g., having a carrier frequency within a range from about 300 MHz to about 8 GHz) to a direct current (DC) power to drive the electrodes 254. Some implementations may provide the capability to regulate the DC power remotely. Some implementations may further provide different amounts of power to different electrodes, as discussed in further detail below.

Figure 7:
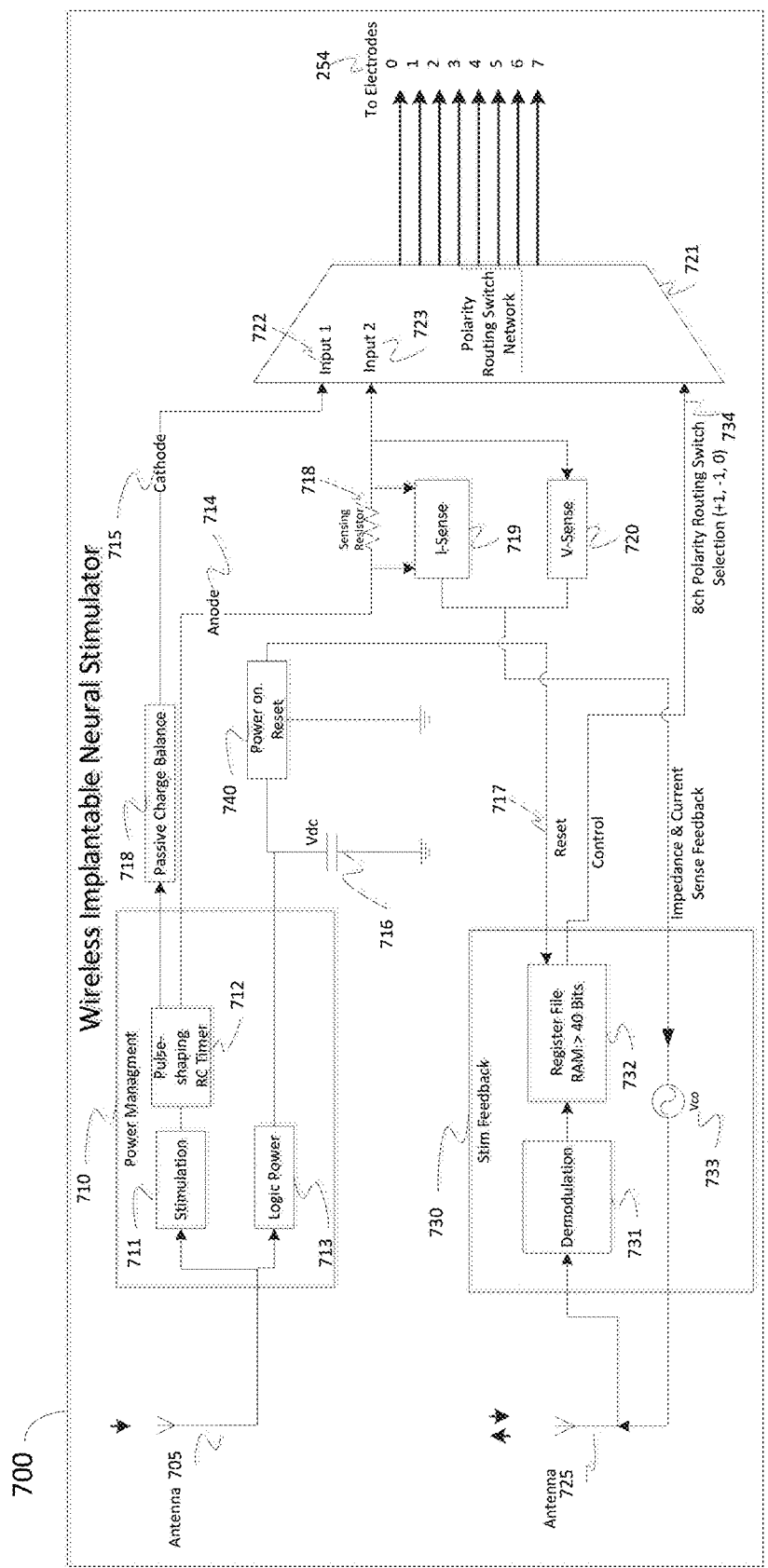
FIG. 7 is a schematic showing an example of a wireless implantable stimulator device with components to implement control and feedback functions.

FIG. 7 is a schematic showing an example of an implantable wireless stimulator device 700 with components to implement control and feedback functions as discussed above in association with FIG. 6. An RX antenna 705 receives the input signal. The RX antenna 705 may be embedded as a dipole, microstrip, folded dipole or other antenna configuration other than a coiled configuration, as described above. The input signal has a carrier frequency in the GHz range and contains electrical energy for powering the wireless implantable stimulator device 700 and for providing stimulation pulses to electrodes 254. Once received by the antenna 705, the input signal is routed to power management circuitry 710. Power management circuitry 710 is configured to rectify the input signal and convert it to a DC power source. For example, the power management circuitry 710 may include a diode rectification bridge such as the diode rectification bridge 402 illustrated in FIG. 4. The DC power source provides power to stimulation circuitry 711 and logic power circuitry 713. The rectification may utilize one or more full wave diode bridge rectifiers within the power management circuitry 710. In one implementation, a resistor can be placed across the output nodes of the bridge rectifier to discharge the electrodes to the ground of the bridge anode, as illustrated by the shunt register 404 in FIG. 7.

Figure 8:
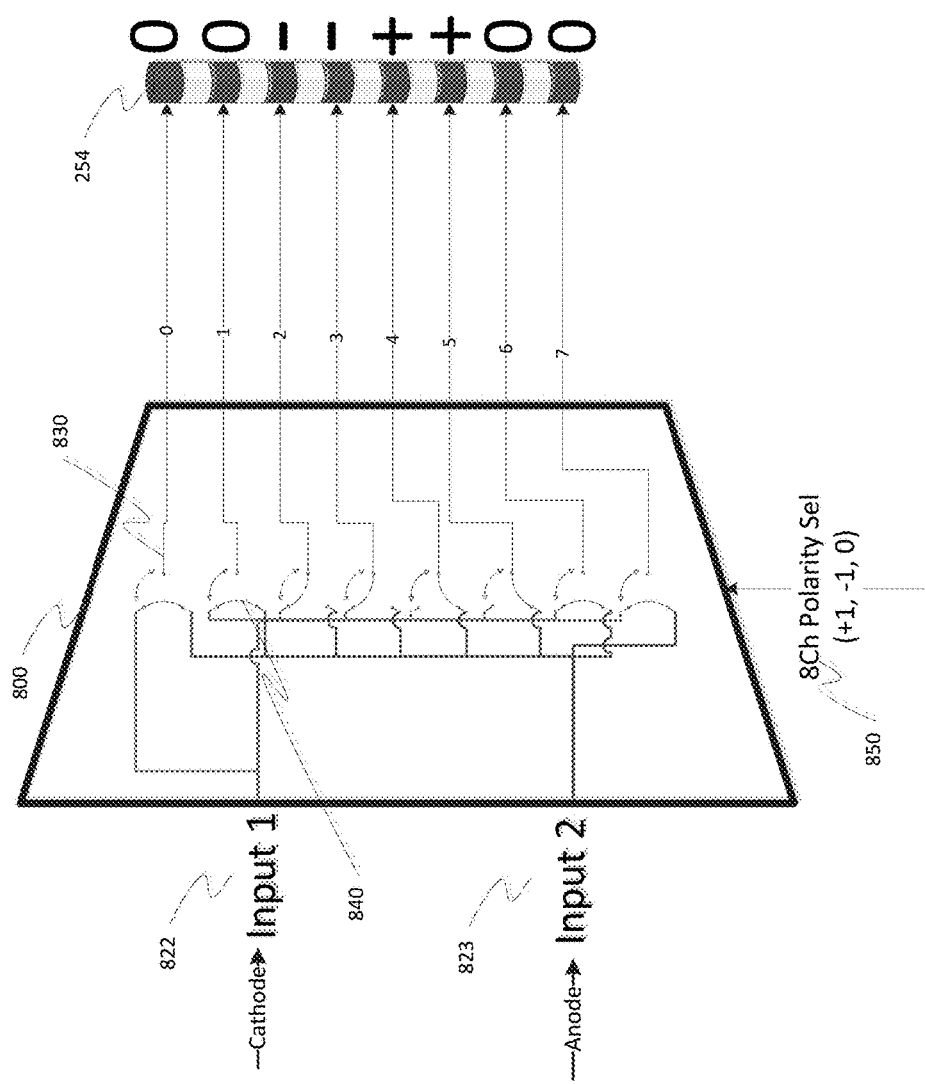
FIG. 8 is a schematic of an example of a polarity routing switch network.

Turning momentarily to FIG. 8, a schematic of an example of a polarity routing switch network 800 is shown. As discussed above, the cathodic (−) energy and the anodic energy are received at input 1 (block 722) and input 2 (block 723), respectively. Polarity routing switch network 800 has one of its outputs coupled to an electrode of electrodes 254 which can include as few as two electrodes, or as many as sixteen electrodes. Eight electrodes are shown in this implementation as an example.

Polarity routing switch network 800 is configured to either individually connect each output to one of input 1 or input 2, or disconnect the output from either of the inputs.

This selects the polarity for each individual electrode of electrodes 254 as one of: neutral (off), cathode (negative), or anode (positive). Each output is coupled to a corresponding three-state switch 830 for setting the connection state of the output. Each three-state switch is controlled by one or more of the bits from the selection input 850. In some implementations, selection input 850 may allocate more than one bits to each three-state switch. For example, two bits may encode the three-state information. Thus, the state of each output of polarity routing switch device 800 can be controlled by information encoding the bits stored in the register 732, which may be set by polarity assignment information received from the remote RF pulse generator module 106, as described further below.

Returning to FIG. 7, power and impedance sensing circuitry may be used to determine the power delivered to the tissue and the impedance of the tissue. For example, a sensing resistor 718 may be placed in serial connection with the anodic branch 714. Current sensing circuit 719 senses the current across the resistor 718 and voltage sensing circuit 720 senses the voltage across the resistor. The measured current and voltage may correspond to the actual current and voltage applied by the electrodes to the tissue.

As described below, the measured current and voltage may be provided as feedback information to RF pulse generator module 106. The power delivered to the tissue may be determined by integrating the product of the measured current and voltage over the duration of the waveform being delivered to electrodes 254. Similarly, the impedance of the tissue may be determined based on the measured voltage being applied to the electrodes and the current being applied to the tissue. Alternative circuitry (not shown) may also be used in lieu of the sensing resistor 718, depending on implementation of the feature and whether both impedance and power feedback are measured individually, or combined.

The measurements from the current sensing circuitry 719 and the voltage sensing circuitry 720 may be routed to a voltage controlled oscillator (VCO) 733 or equivalent circuitry capable of converting from an analog signal source to a carrier signal for modulation. VCO 733 can generate a digital signal with a carrier frequency. The carrier frequency may vary based on analog measurements such as, for example, a voltage, a differential of a voltage and a power, etc. VCO 733 may also use amplitude modulation or phase shift keying to modulate the feedback information at the carrier frequency. The VCO or the equivalent circuit may be generally referred to as an analog controlled carrier modulator. The modulator may transmit information encoding the sensed current or voltage back to RF pulse generator 106.

Antenna 725 may transmit the modulated signal, for example, in the GHz frequency range, back to the RF pulse generator module 106. In some embodiments, antennas 705 and 725 may be the same physical antenna. In other embodiments, antennas 705 and 725 may be separate physical antennas. In the embodiments of separate antennas, antenna 725 may operate at a resonance frequency that is higher than the resonance frequency of antenna 705 to send stimulation feedback to RF pulse generator module 106. In some embodiments, antenna 725 may also operate at the higher resonance frequency to receive data encoding the polarity assignment information from RF pulse generator module 106.

Antenna 725 may include a telemetry antenna 725 which may route received data, such as polarity assignment information, to the stimulation feedback circuit 730. The encoded polarity assignment information may be on a band in the GHz range. The received data may be demodulated by demodulation circuitry 731 and then stored in the register file 732. The register file 732 may be a volatile memory. Register file 732 may be an 8-channel memory bank that can store, for example, several bits of data for each channel to be assigned a polarity. Some embodiments may have no register file, while some embodiments may have a register file up to 64 bits in size. The information encoded by these bits may be sent as the polarity selection signal to polarity routing switch network 721, as indicated by arrow 734. The bits may encode the polarity assignment for each output of the polarity routing switch network as one of: + (positive), − (negative), or 0 (neutral). Each output connects to one electrode and the channel setting determines whether the electrode will be set as an anode (positive), cathode (negative), or off (neutral).

Returning to power management circuitry 710, in some embodiments, approximately 90% of the energy received is routed to the stimulation circuitry 711 and less than 10% of the energy received is routed to the logic power circuitry 713. Logic power circuitry 713 may power the control components for polarity and telemetry. In some implementations, the power circuitry 713, however, does not provide the actual power to the electrodes for stimulating the tissues. In certain embodiments, the energy leaving the logic power circuitry 713 is sent to a capacitor circuit 716 to store a certain amount of readily available energy. The voltage of the stored charge in the capacitor circuit 716 may be denoted as Vdc. Subsequently, this stored energy is used to power a power-on reset circuit 716 configured to send a reset signal on a power-on event. If the wireless implantable neural stimulator 700 loses power for a certain period of time, for example, in the range from about 1 millisecond to over 10 milliseconds, the contents in the register file 732 and polarity setting on polarity routing switch network 721 may be zeroed. The implantable wireless stimulation device 700 may lose power, for example, when it becomes less aligned with RF pulse generator module 106. Using this stored energy, power-on reset circuit 740 may provide a reset signal as indicated by arrow 717. This reset signal may cause stimulation feedback circuit 730 to notify RF pulse generator module 106 of the loss of power. For example, stimulation feedback circuit 730 may transmit a telemetry feedback signal to RF pulse generator module 106 as a status notification of the power outage. This telemetry feedback signal may be transmitted in response to the reset signal and immediately after power is back on wireless stimulation device 700. RF pulse generator module 106 may then transmit one or more telemetry packets to implantable wireless stimulation device. The telemetry packets contain polarity assignment information, which may be saved to register file 732 and may be sent to polarity routing switch network 721. Thus, polarity assignment information in register file 732 may be recovered from telemetry packets transmitted by RF pulse generator module 106 and the polarity assignment for each output of polarity routing switch network 721 may be updated accordingly based on the polarity assignment information.

The telemetry antenna 725 may transmit the telemetry feedback signal back to RF pulse generator module 106 at a frequency higher than the characteristic frequency of an RX antenna 705. In one implementation, the telemetry antenna 725 can have a heightened resonance frequency that is the second harmonic of the characteristic frequency of RX antenna 705. For example, the second harmonic may be utilized to transmit power feedback information regarding an estimate of the amount of power being received by the electrodes. The feedback information may then be used by the RF pulse generator in determining any adjustment of the power level to be transmitted by the RF pulse generator 106. In a similar manner, the second harmonic energy can be used to detect the tissue depth. The second harmonic transmission can be detected by an external antenna, for example, on RF pulse generator module 106 that is tuned to the second harmonic. As a general matter, power management circuitry 710 may contain rectifying circuits that are non-linear device capable of generating harmonic energies from input signal. Harvesting such harmonic energy for transmitting telemetry feedback signal could improve the efficiency of implantable wireless stimulator device 700.

Figure 9A:
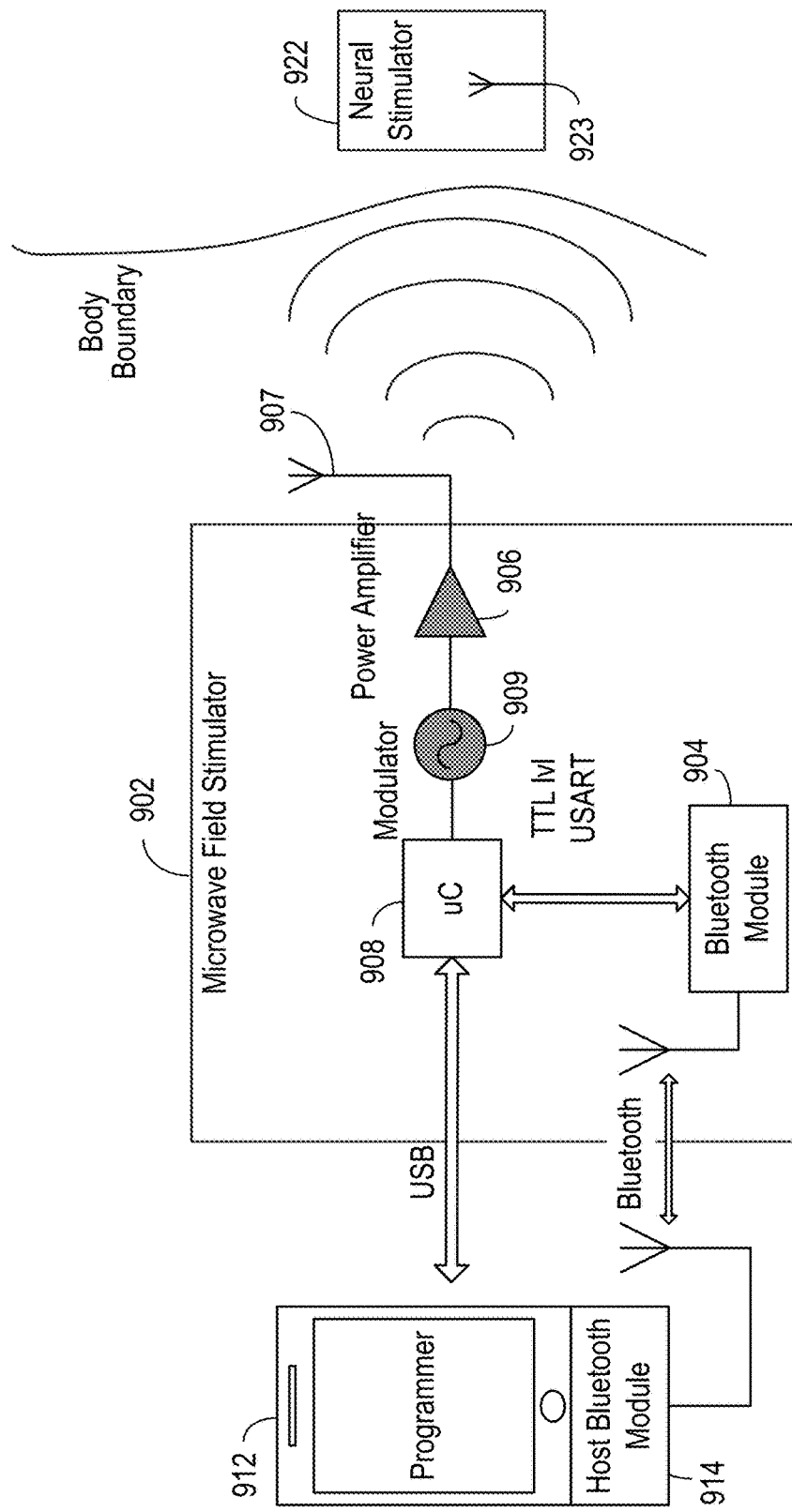
FIG. 9A is a diagram of an example microwave field stimulator (MFS) operating along with a wireless implantable stimulator device.

FIG. 9A is a diagram of an example implementation of a microwave field stimulator (MFS) 902 as part of a stimulation system utilizing an implantable wireless stimulator device 922. In this example, the MFS 902 is external to a patient's body and may be placed within in close proximity, for example, within 3 feet, to an implantable wireless stimulator device 922. The RF pulse generator module 106 may be one example implementation of MFS 902. MFS 902 may be generally known as a controller module. The implantable wireless stimulator device 922 is a passive device. The implantable wireless stimulator device 922 does not have its own independent power source, rather it receives power for its operation from transmission signals emitted from a TX antenna powered by the MFS 902, as discussed above.

In certain embodiments, the MFS 902 may communicate with a programmer 912. The programmer 912 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 904, which communicates with the host bluetooth module 914 within the programmer 912.

The MFS 902 may additionally communicate with wireless stimulator device 922 by transmitting a transmission signal through a Tx antenna 907 coupled to an amplifier 906. The transmission signal may propagate through skin and underlying tissues to arrive at the Rx antenna 923 of the wireless stimulator device 922. In some implementations, the wireless stimulator device 922 may transmit a telemetry feedback signal back to microwave field stimulator 902.

The microwave field stimulator 902 may include a microcontroller 908 configured to manage the communication with a programmer 912 and generate an output signal. The output signal may be used by the modulator 909 to modulate a RF carrier signal. The frequency of the carrier signal may be in the microwave range, for example, from about 300 MHz to about 8 GHz, preferably from about 800 MHz to 1.3 GHz. The modulated RF carrier signal may be amplified by an amplifier 906 to provide the transmission signal for transmission to the wireless stimulator device 922 through a TX antenna 907.

Figure 9B:
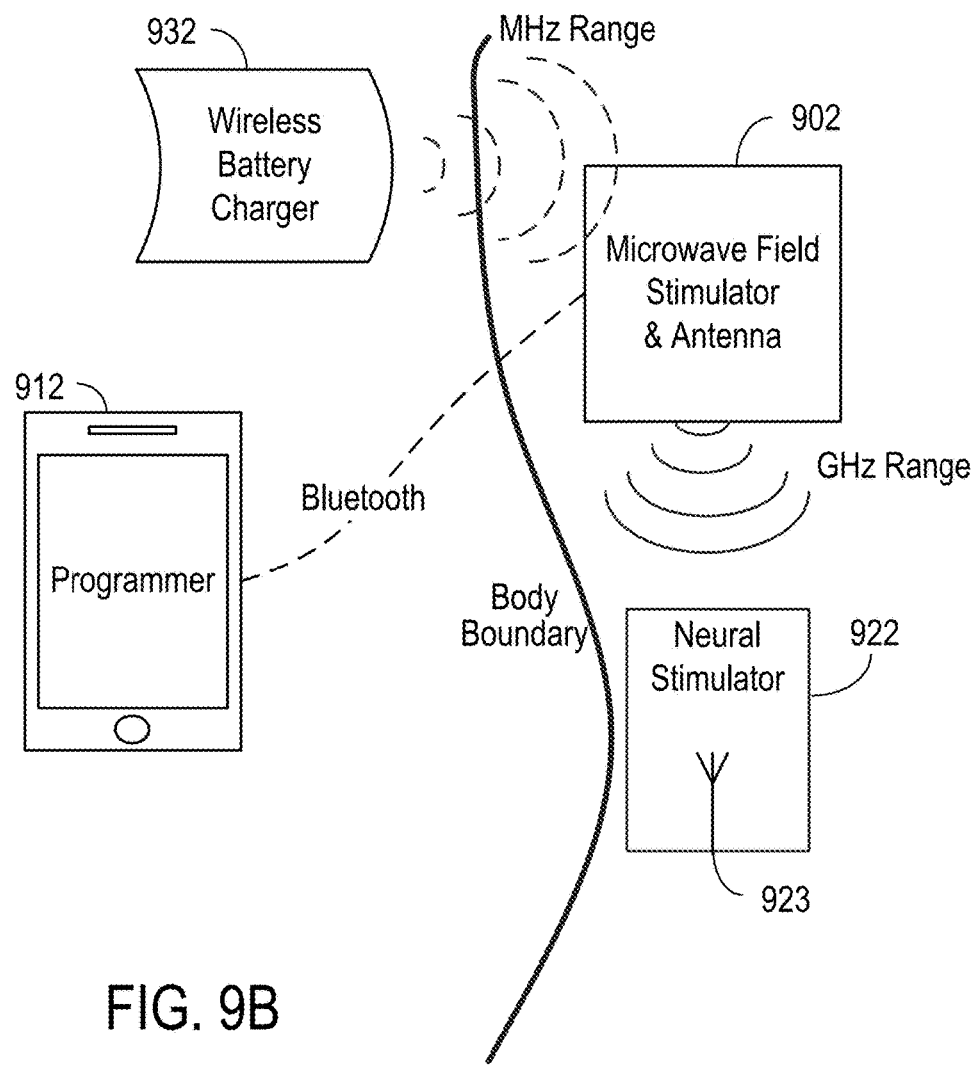
FIG. 9B is a diagram of another example MFS operating along with a wireless implantable stimulator device.

FIG. 9B is a diagram of another example of an implementation of a microwave field stimulator 902 as part of a stimulation system utilizing a wireless stimulator device 922. In this example, the microwave field stimulator 902 may be embedded in the body of the patient, for example, subcutaneously. The embedded microwave field stimulator 902 may receive power from a detached, remote wireless battery charger 932.

The power from the wireless battery charger 932 to the embedded microwave field stimulator 902 may be transmitted at a frequency in the MHz or GHz range. The microwave field stimulator 902 shall be embedded subcutaneously at a very shallow depth (e.g., less than 1 cm), and alternative coupling methods may be used to transfer energy from wireless battery charger 932 to the embedded MFS 902 in the most efficient manner as is well known in the art.

In some embodiments, the microwave field stimulator 902 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the microwave field stimulator 902 shall transmit power and parameter signals to a passive Tx antenna also embedded subcutaneously, which shall be coupled to the RX antenna within the wireless stimulator device 922. The power required in this embodiment is substantially lower since the TX antenna and the RX antenna are already in body tissue and there is no requirement to transmit the signal through the skin.

Figure 10:
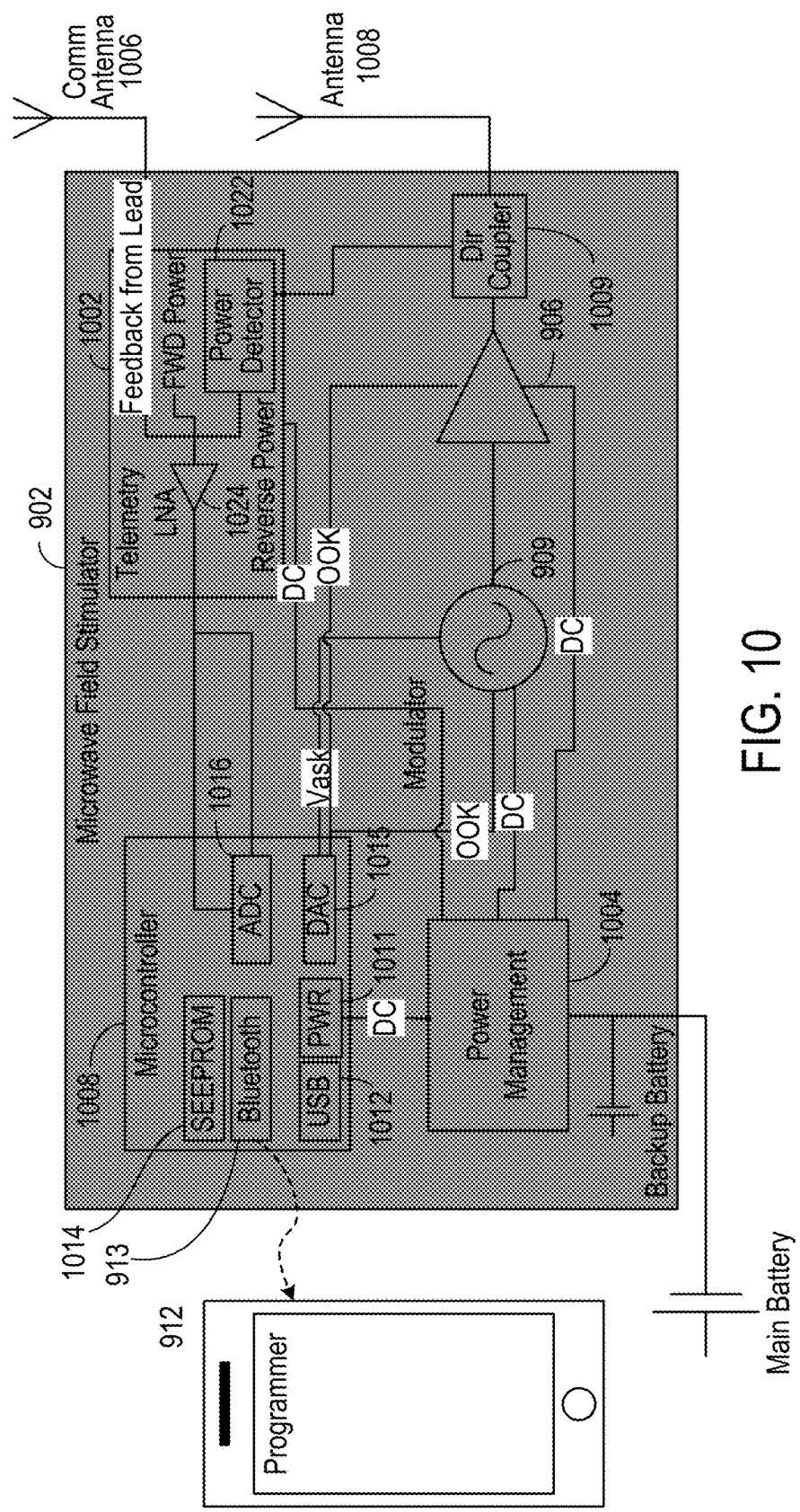
FIG. 10 is a detailed diagram of an example MFS.

FIG. 10 is a detailed diagram of an example microwave field stimulator 902. A microwave field stimulator 902 may include a microcontroller 908, a telemetry feedback module 1002, and a power management module 1004. The microwave field stimulator 902 has a two-way communication schema with a programmer 912, as well as with a communication or telemetry antenna 1006. The microwave field stimulator 902 sends output power and data signals through a TX antenna 1008.

The microcontroller 908 may include a storage device 1014, a bluetooth interface 1013, a USB interface 1012, a power interface 1011, an analog-to-digital converter (ADC) 1016, and a digital to analog converter (DAC) 1015. Implementations of a storage device 1014 may include non-volatile memory, such as, for example, static electrically erasable programmable read-only memory (SEEPROM) or NAND flash memory. A storage device 1014 may store waveform parameter information for the microcontroller 908 to synthesize the output signal used by modulator 909. The stimulation waveform may include multiple pulses. The waveform parameter information may include the shape, duration, amplitude of each pulse, as well as pulse repetition frequency. A storage device 1014 may additionally store polarity assignment information for each electrode of the wireless stimulator device 922. The Bluetooth interface 1013 and USB interface 1012 respectively interact with either the bluetooth module 1004 or the USB module to communicate with the programmer 912.

The communication antenna 1006 and a TX antenna 1008 may, for example, be configured in a variety of sizes and form factors, including, but not limited to a patch antenna, a slot antenna, or a dipole antenna. The TX antenna 1008 may be adapted to transmit a transmission signal, in addition to power, to the implantable, passive neural stimulator device 922. As discussed above, an output signal generated by the microcontroller 908 may be used by the modulator 909 to provide the instructions for creation of a modulated RF carrier signal. The RF carrier signal may be amplified by amplifier 906 to generate the transmission signal. A directional coupler 1009 may be utilized to provide two-way coupling so that both the forward power of the transmission signal flow transmitted by the TX antenna 1008 and the reverse power of the reflected transmission may be picked up by power detector 1022 of telemetry feedback module 1002. In some implementations, a separate communication antenna 1006 may function as the receive antenna for receiving telemetry feedback signal from the wireless stimulator device 922. In some configurations, the communication antenna may operate at a higher frequency band than the TX antenna 1008. For example, the communication antenna 1006 may have a characteristic frequency that is a second harmonic of the characteristic frequency of TX antenna 1008, as discussed above.

In some embodiments, the microwave field stimulator 902 may additionally include a telemetry feedback module 902. In some implementations, the telemetry feedback module 1002 may be coupled directly to communication antenna 1006 to receive telemetry feedback signals. The power detector 1022 may provide a reading of both the forward power of the transmission signal and a reverse power of a portion of the transmission signal that is reflected during transmission. The telemetry signal, forward power reading, and reverse power reading may be amplified by low noise amplifier (LNA) 1024 for further processing. For example, the telemetry module 902 may be configured to process the telemetry feedback signal by demodulating the telemetry feedback signal to extract the encoded information. Such encoded information may include, for example, a status of the wireless stimulator device 922 and one or more electrical parameters associated with a particular channel (electrode) of the wireless stimulator device 922. Based on the decoded information, the telemetry feedback module 1002 may be used to calculate a desired operational characteristic for the wireless stimulator device 922.

Some embodiments of the MFS 902 may further include a power management module 1004. A power management module 1004 may manage various power sources for the MFS 902. Example power sources include, but are not limited to, lithium-ion or lithium polymer batteries. The power management module 1004 may provide several operational modes to save battery power. Example operation modes may include, but are not limited to, a regular mode, a low power mode, a sleep mode, a deep sleep/hibernate mode, and an off mode. The regular mode provides regulation of the transmission of transmission signals and stimulus to the wireless stimulator device 922. In regular mode, the telemetry feedback signal is received and processed to monitor the stimuli as normal. Low-power mode also provides regulation of the transmission of transmission signals and stimulus to the electrodes of the wireless stimulation device. However, under this mode, the telemetry feedback signal may be ignored. More specifically, the telemetry feedback signal encoding the stimulus power may be ignored, thereby saving MFS 902 overall power consumption. Under sleep mode, the transceiver and amplifier 906 are turned off, while the microcontroller is kept on with the last saved state in its memory. Under the deep sleep/hibernate mode, the transceiver and amplifier 906 are turned off, while the microcontroller is in power down mode, but power regulators are on. Under the off mode, all transceiver, microcontroller and regulators are turned off achieving zero quiescent power.

Figure 11:
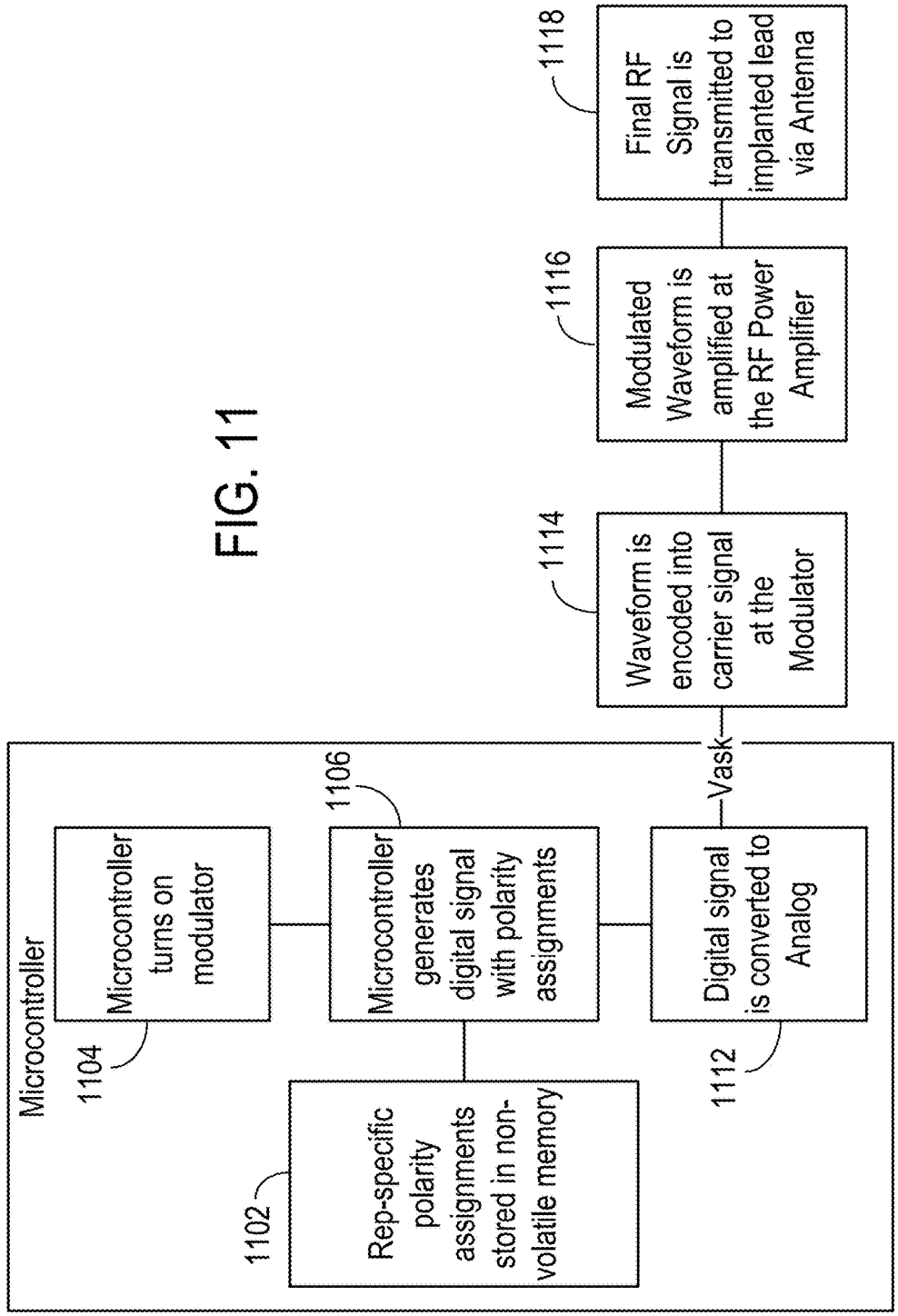
FIG. 11 is a flowchart showing an example process in which the MFS transmits polarity setting information to the wireless implantable stimulator device.

FIG. 11 is a flowchart showing an example process in which the microwave field stimulator 902 transmits polarity setting information to the wireless stimulator device 922. Polarity assignment information is stored in a non-volatile memory 1102 within the microcontroller 908 of the MFS 902. The polarity assignment information may be representative-specific and may be chosen to meet the specific need of a particular patient. Based on the polarity assignment information chosen for a particular patient, the microcontroller 908 executes a specific routine for assigning polarity to each electrode of the electrode array. The particular patient has an wireless stimulation device as described above.

In some implementations, the polarity assignment procedure includes sending a signal to the wireless stimulation device with an initial power-on portion followed by a configuration portion that encodes the polarity assignments. The power-on portion may, for example, simply include the RF carrier signal. The initial power-on portion has a duration that is sufficient to power-on the wireless stimulation device and allow the device to reset into a configuration mode. Once in the configuration mode, the device reads the encoded information in the configuration portion and sets the polarity of the electrodes as indicated by the encoded information.

Thus, in some implementations, the microcontroller 908 turns on the modulator 909 so that the unmodulated RF carrier is sent to the wireless stimulator device 1104. After a set duration, the microcontroller 908 automatically initiates transmitting information encoding the polarity assignment. In this scenario, the microcontroller 908 transmits the polarity settings in the absence of handshake signals from the wireless stimulation device. Because the microwave field stimulator 902 is operating in close proximity to wireless stimulator device 922, signal degradation may not be severe enough to warrant the use of handshake signals to improve quality of communication.

To transmit the polarity information, the microcontroller 908 reads the polarity assignment information from the non-volatile memory and generates a digital signal encoding the polarity information 1106. The digital signal encoding the polarity information may be converted to an analog signal, for example, by a digital-to-analog (DAC) converter 1112. The analog signal encoding the waveform may modulate a carrier signal at modulator 909 to generate a configuration portion of the transmission signal (1114). This configuration portion of the transmission signal may be amplified by the power amplifier 906 to generate the signal to be transmitted by antenna 907 (1116). Thereafter, the configuration portion of the transmission signal is transmitted to the wireless stimulator device 922 (1118).

Once the configuration portion is transmitted to the wireless stimulation device, the microcontroller 908 initiates the stimulation portion of the transmission signal. Similar to the configuration portion, the microcontroller 908 generates a digital signal that encodes the stimulation waveform. The digital signal is converted to an analog signal using the DAC. The analog signal is then used to modulate a carrier signal at modulator 909 to generate a stimulation portion of the transmission signal.

In other implementations, the microcontroller 908 initiates the polarity assignment protocol after the microcontroller 908 has recognized a power-on reset signal transmitted by the neural stimulator. The power-on reset signal may be extracted from a feedback signal received by microcontroller 908 from the wireless stimulator device 922. The feedback signal may also be known as a handshake signal in that it alerts the microwave field stimulator 902 of the ready status of the wireless stimulator device 922. In an example, the feedback signal may be demodulated and sampled to digital domain before the power-on reset signal is extracted in the digital domain.

Figure 12:
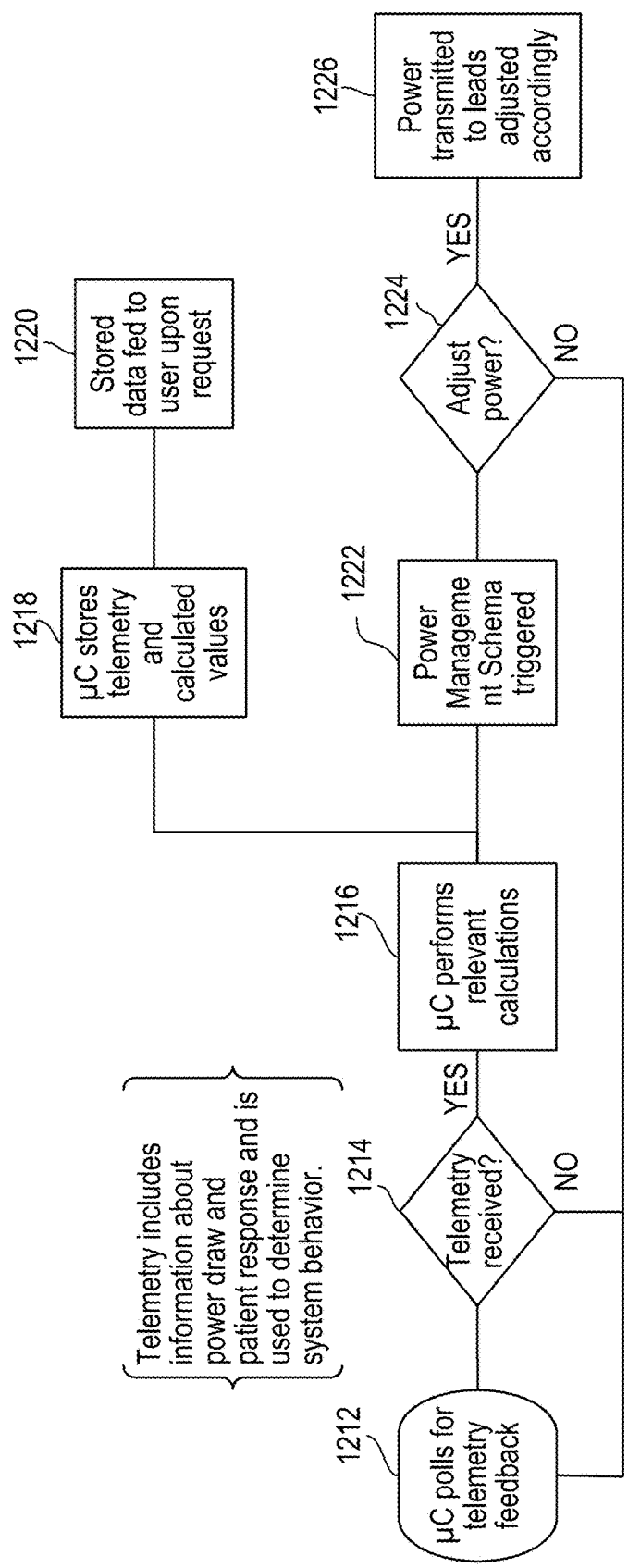
FIG. 12 is another flow chart showing an example process in which the MFS receives and processes the telemetry feedback signal to make adjustments to subsequent transmissions.

FIG. 12 is a flow chart showing an example of the process in which the microwave field stimulator 902 receives and processes the telemetry feedback signal to make adjustments to subsequent transmissions.

In some implementations, the microcontroller 908 polls the telemetry feedback module 1002 (1212). The polling is to determine whether a telemetry feedback signal has been received (1214). The telemetry feedback signal may include information based on which the MFS 902 may ascertain the power consumption being utilized by the electrodes of the wireless stimulator device 922. This information may also be used to determine the operational characteristics of the combination system of the MFS 902 and the wireless stimulator device 922, as will be discussed in further detail in association with FIG. 13. The information may also be logged by the microwave field stimulator 902 so that the response of the patient may be correlated with past treatments received over time. The correlation may reveal the patient's individual response to the treatments the patient has received up to date.

If the microcontroller 908 determines that telemetry feedback module 1002 has not yet received telemetry feedback signal, microcontroller 908 may continue polling (1212). If the microcontroller 908 determines that telemetry feedback module 1002 has received telemetry feedback signal, the microcontroller 908 may extract the information contained in the telemetry feedback signal to perform calculations (1216). The extraction may be performed by demodulating the telemetry feedback signal and sampling the demodulated signal in the digital domain. The calculations may reveal operational characteristics of the wireless stimulator device 922, including, for example, voltage or current levels associated with a particular electrode, power consumption of a particular electrode, and/or impedance of the tissue being stimulated through the electrodes.

Thereafter, in certain embodiments, the microcontroller 908 may store information extracted from the telemetry signals as well as the calculation results (1218). The stored data may be provided to a user through the programmer upon request (1220). The user may be the patient, the doctor, or representatives from the manufacturer. The data may be stored in a non-volatile memory, such as, for example, NAND flash memory or EEPROM.

In other embodiments, a power management schema may be triggered 1222 by the microcontroller (908). Under the power management schema, the microcontroller 908 may determine whether to adjust a parameter of subsequent transmissions (1224). The parameter may be amplitude or the stimulation waveform shape. In one implementation, the amplitude level may be adjusted based on a lookup table showing a relationship between the amplitude level and a corresponding power applied to the tissue through the electrodes. In one implementation, the waveform shape may be pre-distorted to compensate for a frequency response of the microwave field stimulator 902 and the wireless stimulator device 922. The parameter may also be the carrier frequency of the transmission signal. For example, the carrier frequency of the transmission signal may be modified to provide fine-tuning that improves transmission efficiency.

If an adjustment is made, the subsequently transmitted transmission signals are adjusted accordingly. If no adjustment is made, the microcontroller 908 may proceed back to polling the telemetry feedback module 1002 for telemetry feedback signal (1212).

In other implementations, instead of polling the telemetry feedback module 1002, the microcontroller 908 may wait for an interrupt request from telemetry feedback module 1002. The interrupt may be a software interrupt, for example, through an exception handler of the application program. The interrupt may also be a hardware interrupt, for example, a hardware event and handled by an exception handler of the underlying operating system.

Figure 13:
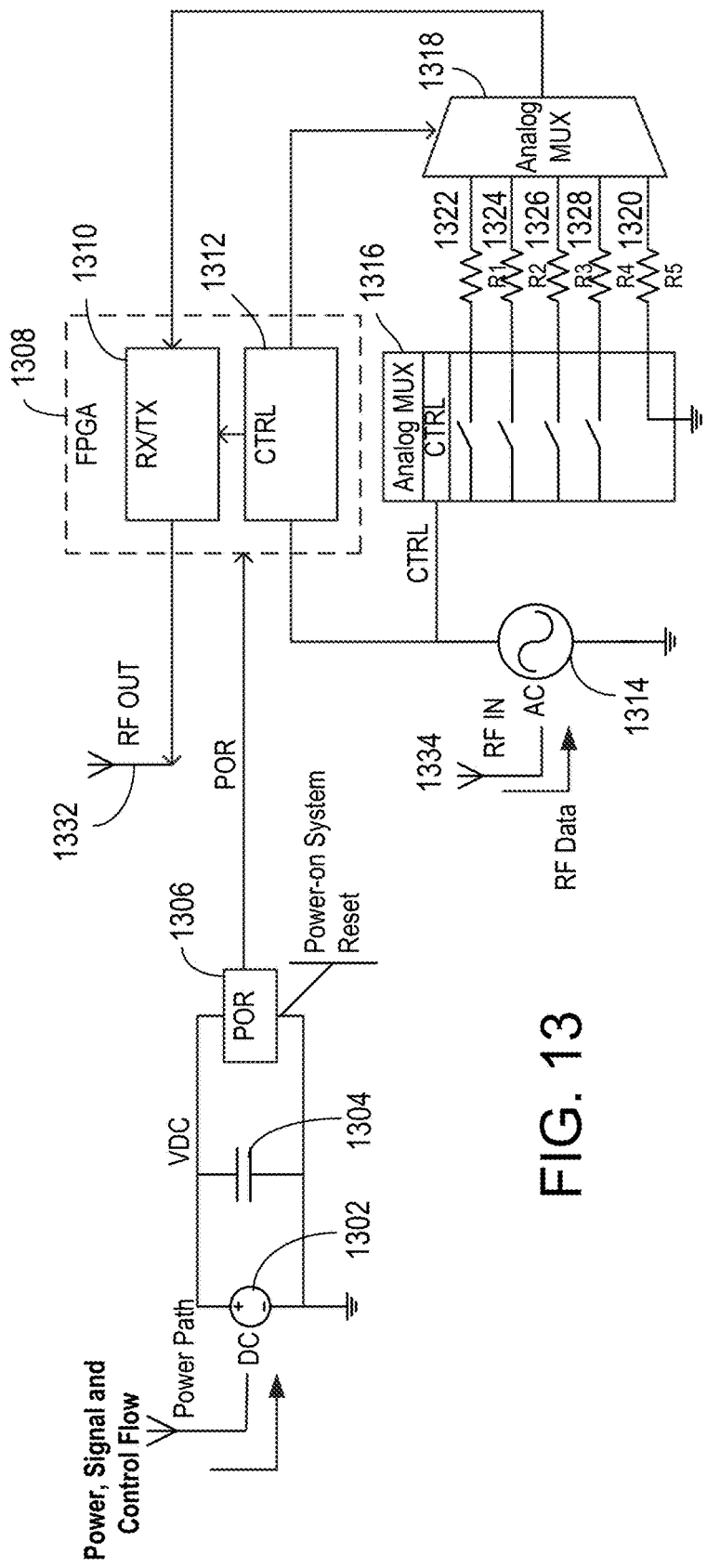
FIG. 13 is a schematic of an example implementation of power, signal and control flow on the wireless implantable stimulator device.

FIG. 13 is a schematic of an example implementation of the power, signal and control flow for the wireless stimulator device 922. A DC source 1302 obtains energy from the transmission signal received at the wireless stimulator device 922 during the initial power-on portion of the transmission signal while the RF power is ramping up. In one implementation, a rectifier may rectify the received power-on portion to generate the DC source 1302 and a capacitor 1304 may store a charge from the rectified signal during the initial portion. When the stored charge reaches a certain voltage (for example, one sufficient or close to sufficient to power operations of the wireless stimulator device 922), the power-on reset circuit 1306 may be triggered to send a power-on reset signal to reset components of the neural stimulator. The power-on set signal may be sent to circuit 1308 to reset, for example, digital registers, digital switches, digital logic, or other digital components, such as transmit and receive logic 1310. The digital components may also be associated with a control module 1312. For example, a control module 1312 may include electrode control 252, register file 732, etc. The power-on reset may reset the digital logic so that the circuit 1308 begins operating from a known, initial state.

In some implementations, the power-on reset signal may subsequently cause the FPGA circuit 1308 to transmit a power-on reset telemetry signal back to MFS 902 to indicate that the implantable wireless stimulator device 922 is ready to receive the configuration portion of the transmission signal that contains the polarity assignment information. For example, the control module 1312 may signal the RX/TX module 1310 to send the power-on reset telemetry signal to the telemetry antenna 1332 for transmission to MFS 902.

In other implementations, the power-on reset telemetry signal may not be provided. As discussed above, due to the proximity between MFS 902 and implantable, passive stimulator device 922, signal degradation due to propagation loss may not be severe enough to warrant implementations of handshake signals from the implantable, passive stimulator device 922 in response to the transmission signal. In addition, the operational efficiency of implantable, passive neural stimulator device 922 may be another factor that weighs against implementing handshake signals.

Once the FPGA circuit 1308 has been reset to an initial state, the FPGA circuit 1308 transitions to a configuration mode configured to read polarity assignments encoded on the received transmission signal during the configuration state. In some implementations, the configuration portion of the transmission signal may arrive at the wireless stimulation device through the RX antenna 1334. The transmission signal received may provide an AC source 1314. The AC source 1314 may be at the carrier frequency of the transmission signal, for example, from about 300 MHz to about 8 GHz.

Thereafter, the control module 1312 may read the polarity assignment information and set the polarity for each electrode through the analog mux control 1316 according to the polarity assignment information in the configuration portion of the received transmission signal. The electrode interface 252 may be one example of analog mux control 1316, which may provide a channel to a respective electrode of the implantable wireless stimulator device 922.

Once the polarity for each electrode is set through the analog mux control 1316, the implantable wireless stimulator device 922 is ready to receive the stimulation waveforms.

Some implementations may not employ a handshake signal to indicate the wireless stimulator device 922 is ready to receive the stimulation waveforms. Rather, the transmission signal may automatically transition from the configuration portion to the stimulation portion. In other implementations, the implantable wireless stimulator device 922 may provide a handshake signal to inform the MFS 902 that implantable wireless stimulator device 922 is ready to receive the stimulation portion of the transmission signal. The handshake signal, if implemented, may be provided by RX/TX module 1310 and transmitted by telemetry antenna 1332.

In some implementations, the stimulation portion of the transmission signal may also arrive at implantable wireless stimulation device through the RX antenna 1334. The transmission signal received may provide an AC source 1314. The AC source 1314 may be at the carrier frequency of the transmission signal, for example, from about 300 MHz to about 8 GHz. The stimulation portion may be rectified and conditioned in accordance with discussions above to provide an extracted stimulation waveform. The extracted stimulation waveform may be applied to each electrode of the implantable wireless stimulator device 922. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings for the corresponding channel.

In some implementations, each channel of analog mux control 1316 is connected to a corresponding electrode and may have a reference resistor placed serially. For example, FIG. 13 shows reference resistors 1322, 1324, 1326, and 1328 in a serial connection with a matching channel. Analog mux control 1316 may additionally include a calibration resistor 1320 placed in a separate and grounded channel. The calibration resistor 1320 is in parallel with a given electrode on a particular channel. The reference resistors 1322, 1324, 1326, and 1328 as well as the calibration resistor 1320 may also be known as sensing resistors 718. These resistors may sense an electrical parameter in a given channel, as discussed below.

In some configurations, an analog controlled carrier modulator may receive a differential voltage that is used to determine the carrier frequency that should be generated. The generated carrier frequency may be proportional to the differential voltage. An example analog controlled carrier modulator is VCO 733.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 1320 and the standard voltage. One example standard voltage may be the ground.

In another configuration, the carrier frequency may reveal an impedance characteristic of a given channel. For example, the differential voltage may be the difference between the voltage at the electrode connected to the channel under measurement and a voltage across the reference resistor in series. Because of the serial connection, a comparison of the voltage across the reference resistor and the voltage at the electrode would indicate the impedance of the underlying tissue being stimulated relative to the impedance of the reference resistor. As the reference resistor's impedance is known, the impedance of the underlying tissue being stimulated may be inferred based on the resulting carrier frequency.

For example, the differential voltage may be the difference between a voltage at the calibration resistor and a voltage across the reference resistor. Because the calibration resistor is placed in parallel to a given channel, the voltage at the calibration is substantially the same as the voltage at the given channel. Because the reference resistor is in a serial connection with the given channel, the voltage at the reference resistor is a part of the voltage across the given channel. Thus, the difference between the voltage at the calibration resistor and the voltage across the reference resistor correspond to the voltage drop at the electrode. Hence, the voltage at the electrode may be inferred based on the voltage difference.

In yet another configuration, the carrier frequency may provide a reading of a current. For example, if the voltage over reference resistor 1322 has been measured, as discussed above, the current going through reference resistor and the corresponding channel may be inferred by dividing the measured voltage by the impedance of reference resistor 1322.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. The telemetry feedback signal may include a signal at the resulting carrier frequency.

The MFS 902 may determine the carrier frequency variation by demodulating at a fixed frequency and measure phase shift accumulation caused by the carrier frequency variation. Generally, a few cycles of RF waves at the resulting carrier frequency may be sufficient to resolve the underlying carrier frequency variation. The determined variation may indicate an operation characteristic of the implantable wireless stimulator device 922. The operation characteristics may include an impedance, a power, a voltage, a current, etc. The operation characteristics may be associated with an individual channel. Therefore, the sensing and carrier frequency modulation may be channel specific and applied to one channel at a given time. Consequently, the telemetry feedback signal may be time shared by the various channels of the implantable wireless stimulator device 922.

In one configuration, the analog MUX 1318 may be used by the controller module 1312 to select a particular channel in a time-sharing scheme. The sensed information for the particular channel, for example, in the form of a carrier frequency modulation, may be routed to RX/TX module 1310. Thereafter, RX/TX module 1310 transmits, through the telemetry antenna 1332, to the MFS 902, the telemetry feedback encoding the sensed information for the particular channel.

Some implementations may include a reconfigurable wireless implantable stimulator device. For example, in some instances, the implantable stimulator device may be placed in a first configuration for transportation and/or placement, and a second configuration for delivering electrical modulation of the excitable tissue.

Figure 14A:
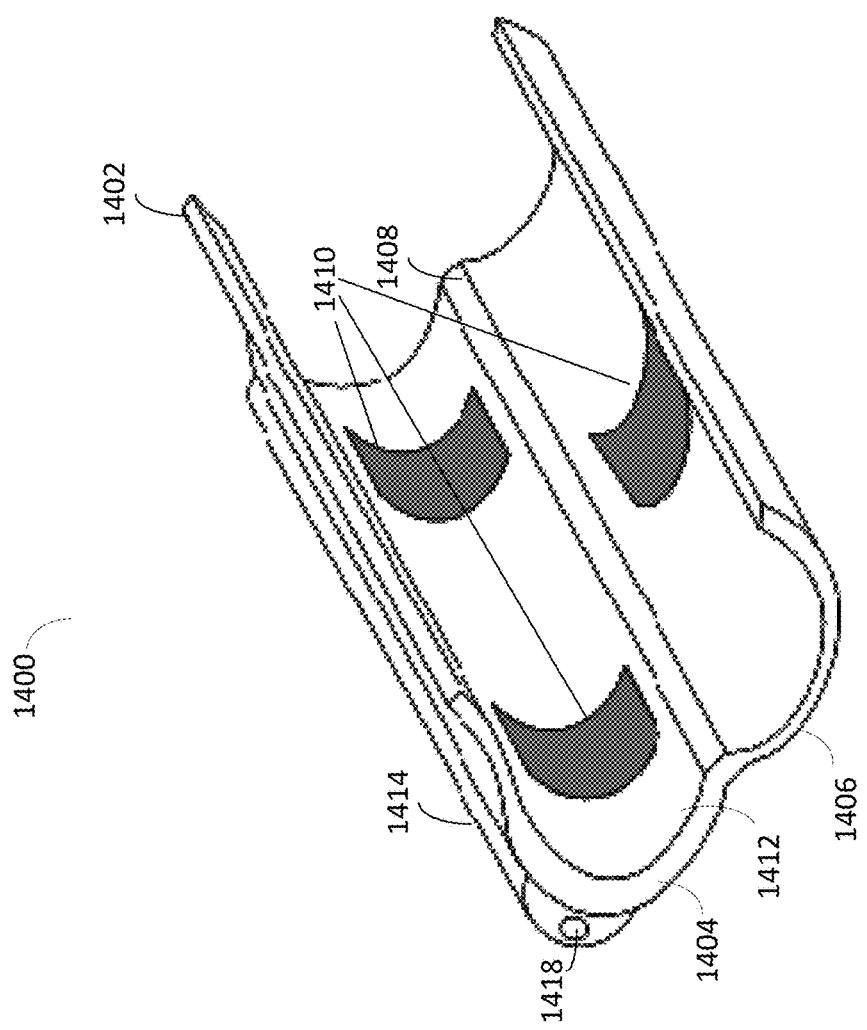
FIG. 14A shows an example of a cylindrical wireless implantable stimulator device in an open configuration.
Figure 14B:
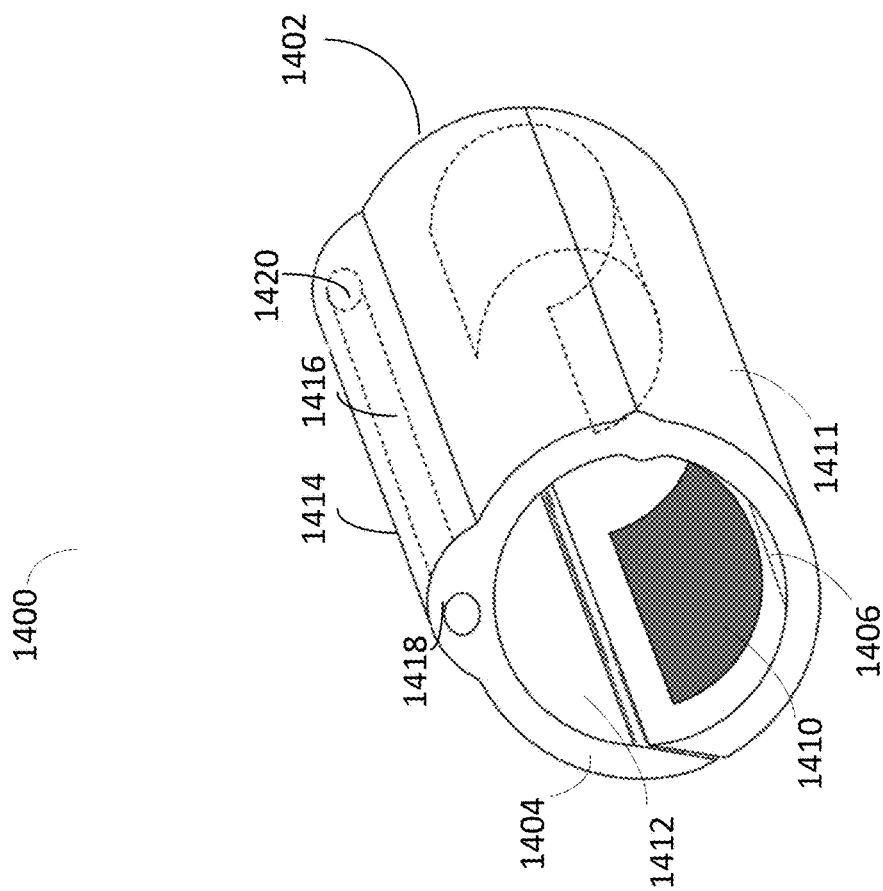
FIG. 14B shows the cylindrical wireless implantable stimulator device in a closed configuration.

Referring now to FIGS. 14A and 14B, an example of a cylindrical wireless implantable stimulator device 1400 includes an implantable stimulator device body 1402. The implantable stimulator device body 1402 includes a first portion 1404 and a second portion 1406 coupled together along a linear hinge 1408. Each of the first portion 1404 and the second portion 1406 includes an outer surface 1411 as well as an inner surface 1412. Electrodes 1410 are mounted on the inner surface 1412. In some instances, the stimulator device body 1402 is encapsulated with a flexible biocompatible material, such as polyurethane, silicon or similar materials.

Both first portion 1404 and second portion 1406 can pivot relative to one another around hinge 1408 between an open position (or configuration) and a closed position (or configuration). In the open position shown in FIG. 14A, the stimulator device body 1402 is configured with first portion 1404 and second portion 1406 open. In this position, first portion 1404 and second portion 1406 may not form an enclosure to surround an anatomical structure.

In the closed position shown in FIG. 14B, the stimulator device body 1402 may be configured as first portion 1404 and second portion 1406 engage each other to form an enclosure that substantially surrounds an anatomical structure, including an excitable tissue such as a nerve. As illustrated, first portion 1404 and second portion 1406 each have a semi-circular cross-sectional shape and, accordingly, when placed in the closed position the stimulator device body 1402 forms a hollow, cylindrical shape. In some instances the enclosure can function as a cage with gaps (not shown) on outer surface 1411. The gaps may improve meshing the implantable stimulator device into the surrounding tissue. In some instances, first portion 1404 and second portion 1406 may not need to contact each other and the enclosure may not be completely closed to form the hollow cylindrical space.

As noted, electrodes 1410 are mounted on the inside of the stimulator device body 1402, i.e., inner surface 1412. Electrodes 1410 may include directional electrodes that apply stimulating current in one direction. Electrodes 1410 may include a multitude of electrodes (e.g., 2-20). In some examples, electrodes 1410 may preferably include around 2-8 electrodes and more preferably 2-4 electrodes. In some examples, electrodes 1410 may preferably include a biocompatible material, such as MP35N, platinum, platinum-iridium or the similar materials. The electrodes 1410 may be curved in a concave shape for applying one or more electrical impulses to a targeted nerve being surrounded by the stimulator device body 1402. The polarities on these directional electrodes can be set such that the stimulation pattern resulting from discharging current is tailored towards the excitable tissue. Applying electrical impulses from within the enclosure can significantly improve stimulation efficiency when the enclosure substantially surrounds the excitable tissue. The use of directional electrodes can further channel the discharging current from the inner surface to the enclosed excitable tissue.

Figure 16A:
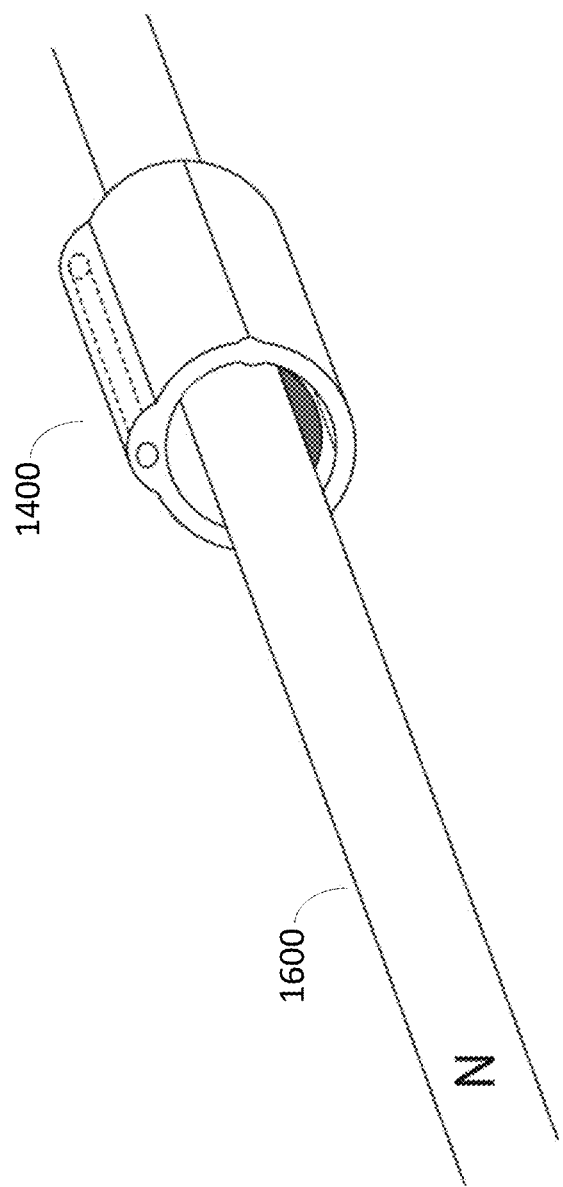

Referring to FIGS. 16A and 16B, a cylindrical wireless implantable stimulator device 1400 is in the closed configuration and placed around a nerve 1600. As shown, cylindrical wireless implantable stimulator device 1400 completely surrounds nerve 1600 such that directional electrodes 1410 (shown in FIGS. 14A and 14B) may apply one or more electrical impulses to encompass the nerve 1600. The cylindrical configuration of the wireless stimulator device allows for a natural wrap-around over the target nerve. With directional electrodes placed on the inside of the wireless stimulator device, precise targeting of the nerve can be achieved with efficiency, thereby reducing the overall power requirements of cylindrical wireless implantable stimulator device 1400 because the chances are reduced for adjacent tissue, nerves or muscles to be stimulated by the electrical impulses. As illustrated in FIG. 16B, the inner surface 1412 of cylindrical wireless implantable stimulator device 1400 is close to but separated from nerve 1600. In some instances, the separation distances between cylindrical wireless implantable lead and nerve 1600 may be between 25 µm to 500 µm. The proximity and separation also facilitates efficient target of the surrounded excitable tissue. Once folded, example cylindrical wireless implantable stimulator device 1400 may be 1.2 mm or less in diameter.

Figure 14C:
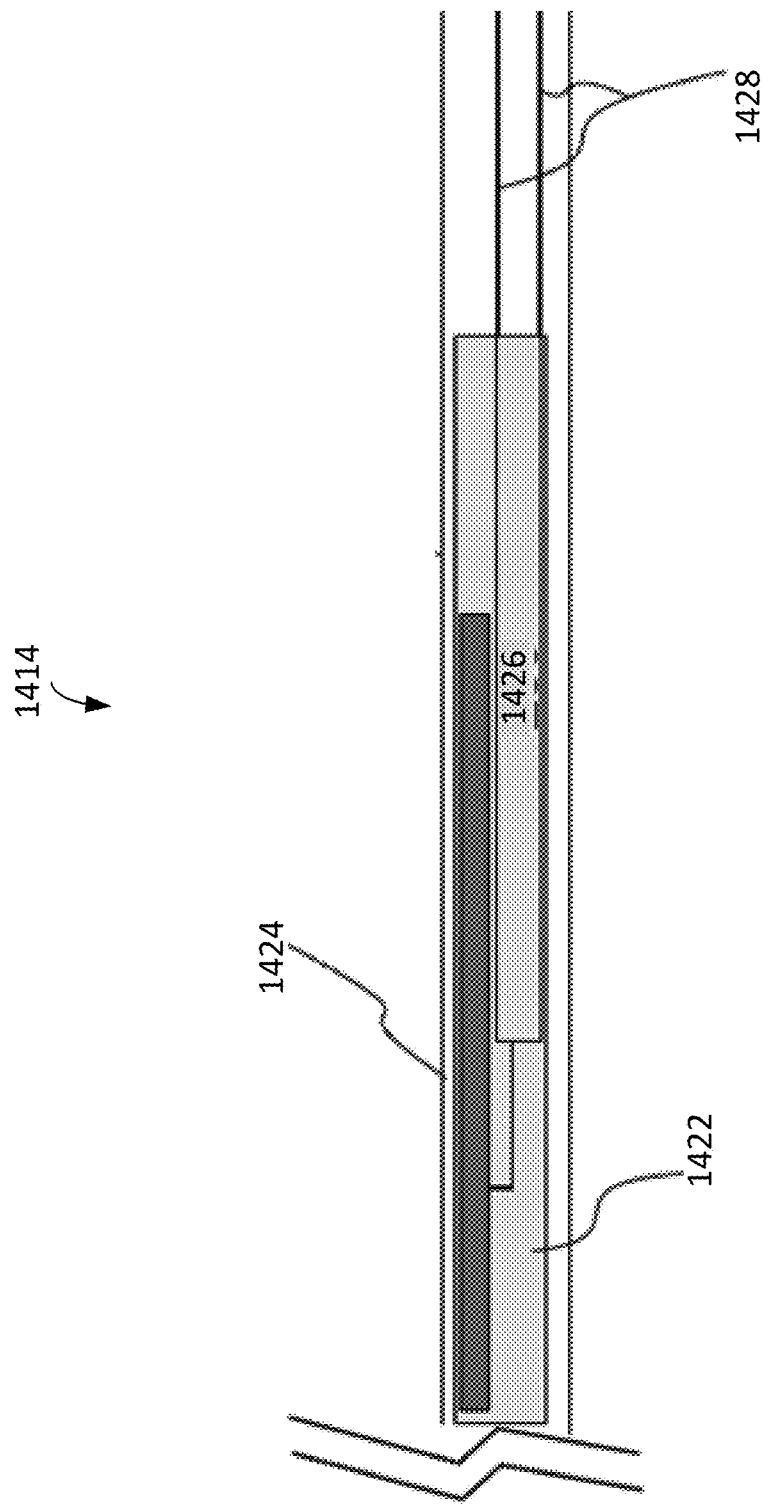
FIG. 14C shows an example of an extension tube of the cylindrical wireless implantable stimulator device.

Returning to FIGS. 14A and 14B, the stimulator device body 1402 further may include an extension tubing 1414 located on the outer surface 1411 and extending parallel to a longitudinal axis of the stimulator device body 1402. In some instances, the extension tube 1414 can be located on the outer surface 1411 of first portion 1404. In other instances, the extension tube 1414 may be located on the outer surface 1411 of second portion 1406. As illustrated, extension tubing 1414 includes an inner lumen 1416 with proximal opening 1418 and distal opening 1420. FIG. 14C illustrates an example of extension tube 1414. One or more receiving antennas 1424 may be located within lumen. The receiving antennas 1424 can include dipole antennas in electrical radiative coupling with transmitting antennas located outside the patient's body (e.g., on an external controller). The receiving antennas 1424 may also include patch antennas. The receiving antennas 1424 can be loopless and non-inductive. The receiving antennas 1424 can capture transmissions of an input signal from the external transmit antenna through electrical radiative coupling. In some instances, the receiving antennas 1424 on wireless implantable stimulator device 1400 may be located 10 cm or more underneath a patient's skin and away from the transmitting antenna on the external controller. In one example, the control device may be configured to transmit the input signal to the targeted site tissue inside the patient's body within 12 cm of skin surface of the patient. The input signal may contain electrical energy to power the wireless implantable stimulator device 1400, as well as waveform parameters specifying particular waveforms for the electrical impulses to be applied at the electrodes 1410. The input signal may have a carrier frequency between about 800 KHz and 5.8 GHz. The waveform parameters may encode electrical impulses having a frequency of 10,000 Hz or less, a pulse width of 1 ms or less. In certain implementations, the frequency may be between about 1-250 Hz. In some instances, the waveform parameters may encode electrical impulses with a frequency from about 10 to 500 Hz. In some instances, the electrical impulses can have a duty cycle of less than 10%.

In some instances, extension tube 1414 may also house circuitry 1426. In these cases, the circuitry 1426 may allow wireless implantable stimulator device 1400 to process the input signal received from a transmitting antenna (also not shown). As described in detail above, the circuitry 1426 may harvest electrical energy contained in the input signal to power the wireless implantable stimulator device 1400. The circuitry 1426 may also extract waveform parameters from the input signal and create electrical impulses suitable for modulation of the excitable tissue through electrodes 1410. The electrical impulses can be created according to the extracted waveform parameters and based on the electrical energy in the input signal. In some instances, the input signal may further include polarity setting information for each electrode on the wireless implantable stimulator device 1400. The circuitry 1426 may extract the polarity setting information from the input signal and set the polarities for each electrode interface accordingly.

In some instances, receiving antennas 1424 and circuitry 1426 may be formed on a flexible circuit 1422 (also known as a flex circuit 1422). The flex circuit 1422 may also include wires 1428 that connect, for example, circuitry 1426 to the electrodes 1410. Wires 1428 can also connect receiving antennas 1424 to tissue-exposed small antenna coupling contacts (not shown). These coupling contacts may be made of a conductive cylindrical piece of metal having a diameter of between about 0.2 mm and about 0.6 mm and a thickness of between about 0.2 mm and about 0.6 mm. The coupling contacts may contact tissue and can be embedded into an electrically insulative material.

In some implementations, cylindrical implantable stimulator device 1400 may further include recording electrodes capable of sensing, for example, neural activities of the excitable tissue. The recording electrodes may also measure the parameters of electrical impulses applied at the electrodes. In these implementations, the circuitry housed in extension tubing 1414 may further include electronics for recording the sensed information and parameters regarding the electrical impulses as applied to the targeted excitable tossing, such as a nerve. The recording/sensing electrodes may be separate from the stimulation electrodes 1410 or they may be the same electrodes that are used for the stimulation. The sensed parameters are transmitted wirelessly (for example, through electrical radiative coupling as discussed above) to antennas (not shown) outside of the patient's body. In some implementations, an external controller (not shown), such as the microwave field stimulator discussed above, may receive the sensed parameters from wireless implantable stimulator device 1400 and may the input signal based on those sensed parameters. The adjusted input signal is then sent back to the receiving antennas within the stimulator device body 1402 such that the electrical impulses may be adjusted in a closed-loop fashion.

Figure 15:
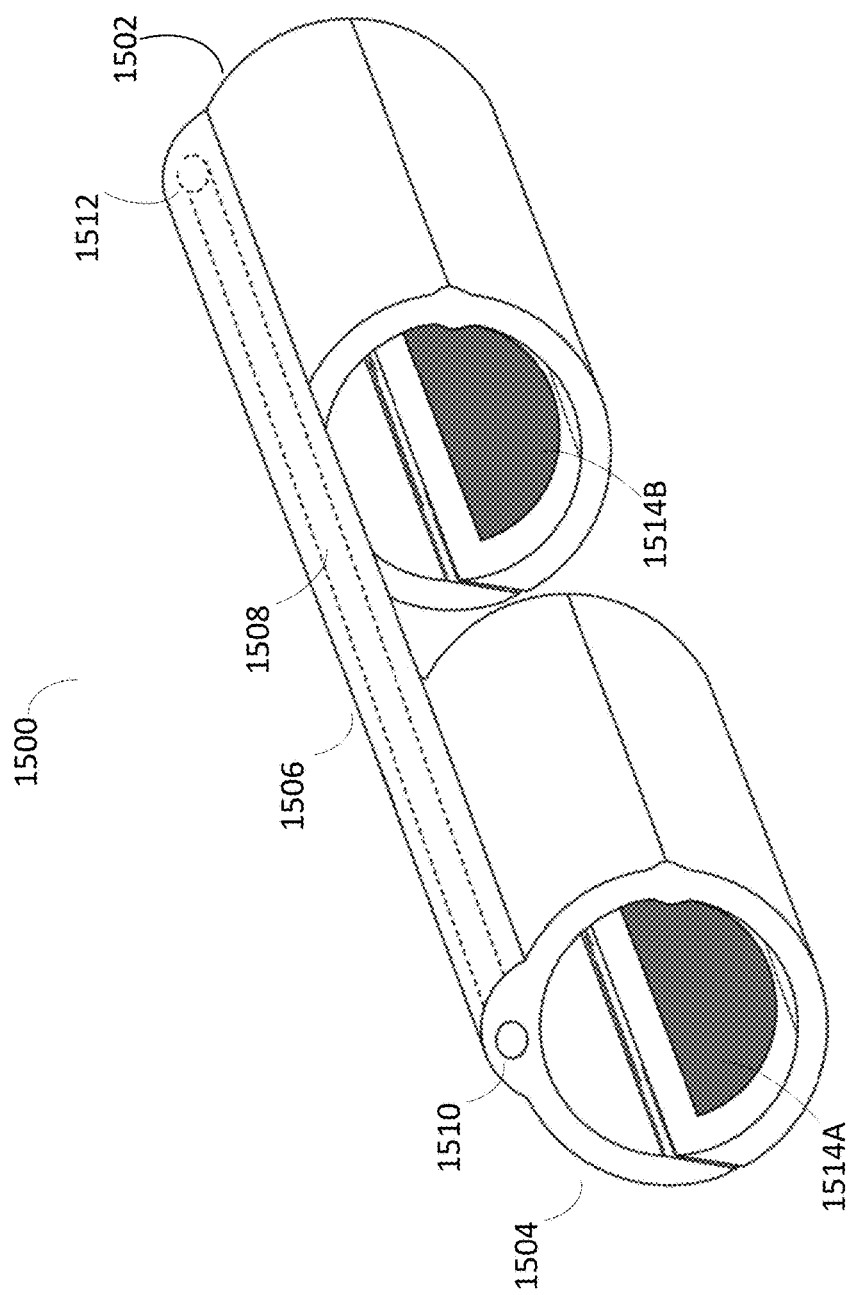
FIG. 15 shows another example of a cylindrical wireless implantable stimulator device with two cuffs.

Some implementations of the cylindrical wireless implantable stimulator device include a one cuff structure, as discussed and illustrated above. Other implementations can include multiple cuff structures. Referring now to FIG. 15, the wireless implantable stimulator device 1500 includes two separate device bodies 1502, 1504 coupled to each other through an extension tubing 1506. The extension tubing 1506 is located on the outer surfaces 1511A and 1511B. The extension tubing 1506 extends from a proximal end of stimulator device body 1502 to a distal end of stimulator device body 1504. Stimulator device bodies 1502, 1504 are each constructed substantially similarly to the stimulator device body 1402 described above and illustrated in FIGS. 14A and 14B. Extension tubing 1506 includes an inner lumen 1508 with openings 1510 on the outer surface 1511A of stimulator device body 1502, as well as opening 1512 on the outer surface 1511B of stimulator device body 1504. In some instances, one or more receiving antennas (not shown) are located within lumen 1508. As discussed above, the receiving antennas can include dipole antennas or patch antennas in electrical radiative coupling with transmit antennas located outside the patient's body (e.g., on an external controller). The receiving antennas can capture transmissions of an input signal from the external transmit antenna through electrical radiative coupling. The input signal may contain electrical energy, waveform parameters, and polarity setting information for both stimulator device bodies 1502 and 1504. In some instances, 1508 may house circuitry for processing the input signal. The circuitry may harvest electrical energy contained in the input signal to power the wireless implantable stimulator device 1500 including stimulator device bodies 1502 and 1504. The circuitry may also extract waveform parameters from the input signal and create electrical impulses suitable for modulation of the excitable tissue through electrodes 1514A on the stimulator device body 1502 or electrodes 1514B on the stimulator device body 1504. The electrical impulses can be created according to the extracted waveform parameters intended to a particular stimulator device body. In some instances, the input signal may further include polarity setting information for each electrode on a particular stimulator device body. The circuitry may extract the polarity setting information from the input signal and set the polarities for each electrode interface accordingly. For example, the circuitry may include switch banks with each switch bank coupled to a particular stimulator device body. In this example, the switch banks can enable polarity setting at the granularity of a given electrode on a particular stimulator device body. As illustrated in FIG. 15, stimulator device bodies 1502 and 1504 are shown in a closed configuration for during transition to the targeted implantation site and for anchoring around the targeted implantation site. The details of the implantation procedures are discussed below in association with FIGS. 17 and 18.

Figure 17:
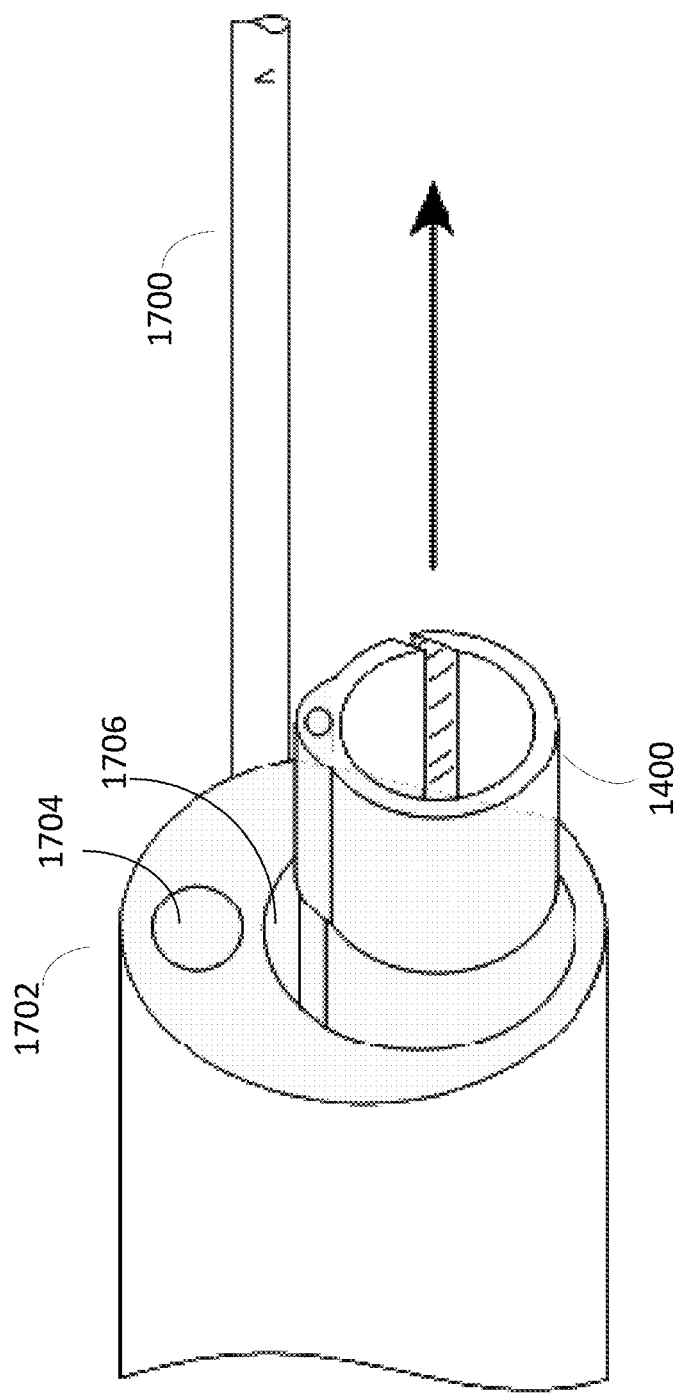
FIG. 17 illustrates an example of the placement of a cylindrical wireless implantable stimulator device through an introducer.

Referring now to FIG. 17, a method for implanting wireless implantable stimulator device 1400 to apply neural modulation on target nerve 2100 in a patient will now be described. As shown, an introducer 1702, such as a cannula, is advanced to a target implantation site within the patient and adjacent to the nerve 1700. In some cases, introducer 1702 may be inserted through a percutaneous penetration in the patient, through an endoscopic opening in the patient, or directly in an open surgical procedure. In some instances, the placement of the introducer 1702 within the patient's body may be under imaging guidance, including for example, X-Ray fluoroscopy or ultrasound fluoroscopy. In certain instances, the placement of introducer 1702 may be aided by, for example, a camera device mounted in the instrument channel 1704 of introducer 1702. Once the distal opening introducer 1702 is positioned adjacent nerve 1700, wireless implantable stimulator device 1400 may be positioned in a closed configuration and into inner lumen 1706 of the introducer 2102. Wireless implantable stimulator device 1400 may then be advanced through inner lumen 1706 until the implantable stimulator device exits distal opening. Introducer 1702 will preferably be positioned such that wireless implantable stimulator device 1400 is substantially coaxial with nerve 1700, as is shown in FIG. 17.

Upon exiting the distal opening of introducer 1702, wireless implantable stimulator device 1400 may be reconfigured into the open configuration where first portion 1404 and second portion 1406 extend to disengage each other (as shown in FIG. 14A). In some instances, first portion 1404 and second portion 1406 may pivot around hinge 1408 to expand into the open configuration in which the first portion 1404 and the second portion 1406 are positioned to wrap around nerve 1700. In these instances, first portion 1404 and second portion 1406 of stimulator device body 1402 may be pivoted back into the closed configuration (shown in FIG. 14B) to form an enclosure that substantially surrounds nerve 1700 (as illustrated in FIGS. 16A and 16B). Thereafter, wireless implantable stimulator device 1700 may be anchored to tissue surrounding nerve 1700, for example, through suturing.

Once wireless implantable stimulator device 1400 is suitable positioned to substantially surround nerve 1700, an input signal can be delivered to one or more receiving antenna(s) (not shown) in extension tubing 1414 of wireless implantable stimulator device 1400 from an external transmitting antenna on a controller located outside of the patient's body. As discussed in detail above, the input signal contains energy and may contain waveform parameters. Circuitry within wireless implantable stimulator device 1400 creates one or more electrical impulses using the energy and, when present, according to the waveform parameters. The circuitry also delivers the electrical pulses through directional electrodes 1410 to the excitable tissue 1700 sufficient for neural modulation. For example, the electrical impulses may be sufficient to generate an action potential in the nerve to treat chronic pain or a disorder in the patient.

After the implantable stimulator device has been confirmed as securely anchored at implantation site and the neural modulation has been fined tuned to adjust to the specific needs of the patient, introducer 1702 can be withdrawn.

Figure 18C:
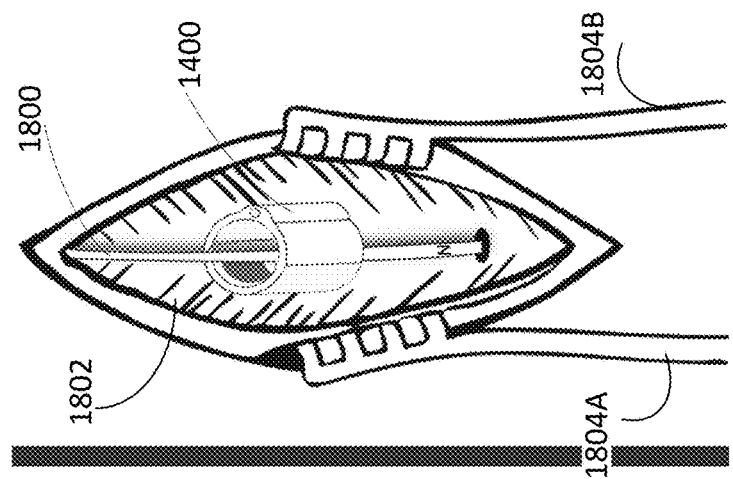
FIGS. 18A to 18C illustrate an example of the placement of a cylindrical wireless implantable stimulator device through surgery.
Figure 18B:
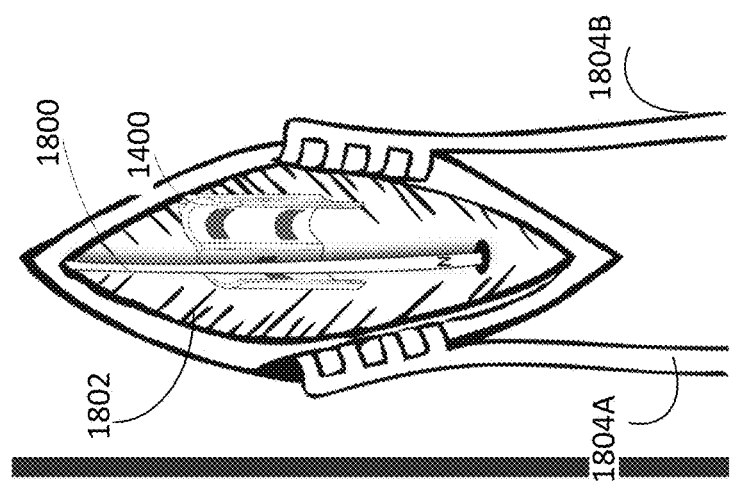
Figure 18A:
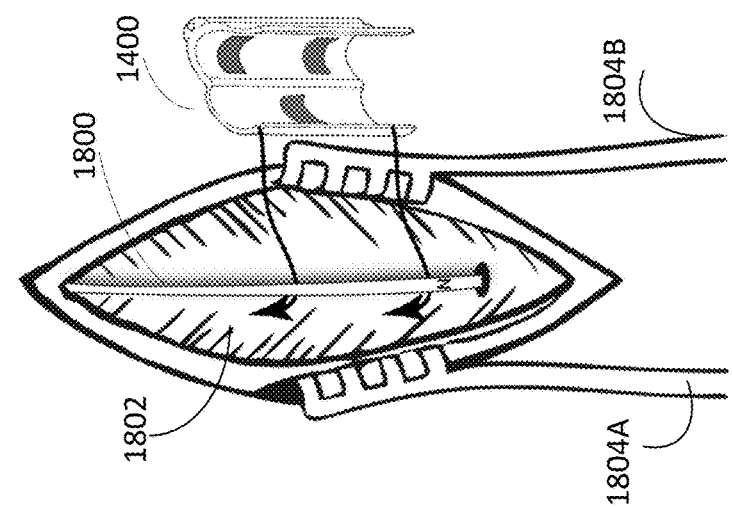

FIG. 18A to 18C show an example of a method for surgical implantation of wireless implantable stimulator device 1400. Initially, a surgical opening may be created on a patient's skin, and spread using retractors 1804A and 1804B. The surgical opening may expose nerve 1800, as illustrated. A surgeon may then determine a segment of the nerve 1800 to be wrapped by wireless implantable stimulator device 1400. Holding the wireless implantable stimulator device 1400 in forceps, the surgeon may place the implantable stimulator device 1400 in an open configuration (as shown in FIG. 14A) and position the implantable stimulator device adjacent to the determined segment of exposed nerve 1800. In some implementations, the positioning may include attempting to wrap the unfolded wireless implantable stimulator device around the target segment from behind nerve 1800, as illustrated in FIG. 18B. Once the wireless stimulator device 1400 is in position, the surgeon may fold first portion 1404 and second portion 1406 by pivoting both portions around hinge 1408. The two portions, once folded to engage each other, can form an enclosure that substantially surrounds target nerve 1800, as shown in FIG. 18C. Thereafter, the surgeon may test the implanted wireless stimulator device 1400 by sending test input signals from an external controller such as the microwave field stimulator disclosed herein. Using test signals, the positioning of wireless stimulator device 1400 may be further adjusted. Once the position of wireless stimulator device 1400 is finalized, the surgeon may anchor wireless stimulator device 1400 to surrounding tissues and withdraw instruments 1804A and 1804B. Thereafter, the surgeon may close the opening by surgical glues, sutures, or stitches.

Referring now to FIG. 19A to 19C, a helical wireless implantable stimulator device 1900 may include a helical portion 1902 coupled tubing linear portion 1904. In some examples, helical wireless implantable stimulator device 1900 may be 1.2 mm or less in diameter. Helical portion 1902 may form an enclosure that can substantially surround an anatomical structure. As shown in FIG. 19B, flexible wires 1910 are placed inside the helical portion 1902 and run the length of helical portion 1902. Flexible wires 1910 may include a biocompatible material, such as nitinol, MP35N, stainless steel or similar materials. The flexible wires 1910 are formed such that they normally take on a helical shape and, accordingly, the flexible wires 1910 cause the helical portion 1902 to take one a helical shape when not biased by an outside force. In other implementations, the helical shape may be formed by molding the helical portion 1602 around the shape of a cylinder and causing the helical portion to retain its shape once molded.

The inner surface of helical portion 1902 may include electrodes 1908A, 1908B, 1908C, and 1908D. Here, the inner surface refers to the surface on the inside of the spiral shape formed by helical portion 1902. These electrodes may include directional electrodes. In some instances, these electrodes may also include recording electrodes to sense neural activities of surrounding neural tissues or to measure waveform parameters as applied on the electrodes.

As illustrated in FIG. 19A, linear portion 1904 includes an instrument lumen 1906 housing electronics block 1907. Instrument lumen 1906 may include one or more orbital lumens in the linear portion 1904. Orbital lumens may be away from the center of linear portion 1904. Orbital lumens may also be known as side lumens. Such instrument lumens generally may not extend the full length of the linear portion 1904. Electronics block 1907 may include one or more receiving antennas and circuitry. In one example, electronics block 1907 may be flat and placed inside instrument lumen 1906. In another example, electronics block 1907 may be curved and fit around instrument lumen 1906 and yet inside linear portion 1904. In some instances, electronics block 1907 may include wires connecting the receiving antennas to the circuitry. In these instances, the wires can also connect the receiving antennas to antenna coupling contracts. These coupling contacts may be made of a conductive cylindrical piece of metal having a diameter of between about 0.2 mm and about 0.6 mm and a thickness of between about 0.2 mm and about 0.6 mm. The coupling contacts may contact tissue and can be embedded into an electrically insulative material. As discussed above, the receiving antennas can include dipole antennas or patch antennas in electrical radiative coupling with transmit antennas located outside the patient's body (e.g., on an external controller). The receiving antennas can capture transmissions of an input signal from the external transmit antenna through electrical radiative coupling. The input signal may contain electrical energy, waveform parameters, and polarity setting information for wireless implantable stimulator device 1900. Instrument lumen 1906 may also house circuitry coupling the receiving antenna(s) to electrodes 1908A to 1908D on helical portion 1902, as discussed above. The circuitry may harvest electrical energy contained in the input signal to power the wireless implantable stimulator device 1900. The circuitry may also extract waveform parameters from the input signal and create electrical impulses suitable for modulation of the excitable tissue through electrodes 1908A to 1908D. The electrical impulses can be created according to the extracted waveform parameters. In some instances, the input signal may further include polarity setting information for each electrode. The circuitry may extract the polarity setting information from the input signal and set the polarities for each electrode interface accordingly. In implementations where some electrodes are recording electrodes, the circuitry can also encode the sensed information of neural activities or measured waveform parameters. In these implementations, the circuitry may then transmit the encoded information to the external controller as a telemetry feedback signal. In some instances, the controller may adjust subsequent transmissions of the input signal to adjust nerve modulation through electrodes 1908A to 1908B in a closed-loop fashion.

As illustrated in FIGS. 19B and 19C, helical wireless implantable stimulator device 1900 may include a stylet lumen 1908. A stylet 1912 can be placed inside stylet lumen 1908. The stylet 1912 generally has a stronger tension than shaping (flexible) wires 1910. Once placed inside stylet lumen 1908 and advanced into helical portion 1902, the stylet 1912 can override the flexible wires 1910 in shaping the helical portion 1902 into a substantially linear configuration. Hence, helical portion 1902 is configured to be transformable between a substantially linear shape shown in FIG. 19C) and a substantially helical shape shown in FIGS. 19A and 19B.

Referring now to FIGS. 20A-C, an example of a method for modulating a nerve 2000 with helical implantable stimulator device 1900 will now be described. As shown in FIG. 20A, an introducer 2002, such as a cannula, is advanced into a position adjacent target nerve 2000. In some cases, introducer 2002 may be inserted through a percutaneous penetration in the patient, through an endoscopic opening in the patient, or directly in an open surgical procedure. In some instances, the placement of the introducer 2002 within the patient's body may be under imaging guidance, including for example, X-Ray fluoroscopy or ultrasound fluoroscopy. In certain instances, the placement of introducer 2002 may be aided by, for example, a camera device mounted in the instrument channel 2004 of introducer 2002. For example, introducer 2002 can be positioned such that its distal opening is adjacent to, and substantially parallel with, nerve 2000. Once introducer 2002 is in position, helical wireless stimulator device 1900 can be placed through inner lumen 2006 of introducer 2002 into a substantially linear configuration shaped by, for example, stylet 1912 (shown in FIG. 19C) mounted inside inner lumen 2006. Helical wireless stimulator device 1900 may be advanced through inner lumen 2006 and may exit through the distal opening of introducer 2002.

As shown in FIG. 20B, once helical portion 1902 begins to exit distal opening of introducer 2002, the stylet 1912 (shown in FIG. 19C) inside the inner lumen 2006 may be withdrawn and helical portion 1902 may automatically transform into the helical shape such that helical portion 1902 twists and effectively wraps around nerve 2000. When helical wireless stimulator device 1900 is further advanced through inner lumen 2006, the entire helical portion 1902 can exit the distal end of introducer 2002 and wraparound nerve 2000 such that directional electrodes 1908A to 1908D are facing nerve 2000, as illustrated in FIG. 20C. Test input signals may then be applied to confirm that the implantation is successful. Once the implantation has been confirmed as successful, introducer 2002 may be withdrawn such that extension tube 1904 in the linear portion of helical wireless stimulator device 1900 also exits distal opening of introducer 2002. Thereafter, helical wireless stimulator device 1900 may be secured to surrounding tissues so that the helical portion 1902 becomes attached to nerve 2000.

When helical wireless stimulator device 1900 is suitably positioned so that helical portion 1902 substantially surrounds nerve 2000, an input signal can be delivered to one or more receiving antenna(s) in extension tubing 1904 of helical wireless stimulator device 1900 from an external transmitting antenna and controller located outside of the patient's body. As discussed in detail above, the input signal may contain energy, waveform parameters, and polarity setting information. Circuitry within wireless stimulator device 1900 may create electrical impulses for modulating a nerve using the waveform parameters. The electrical impulses can be delivered through directional electrodes 1908A to 1908D to the target nerve for nerve modulation.

Directional electrodes can be used on the inner surface of the cylindrical wireless implantable stimulator device and the helical wireless implantable stimulator device. FIGS. 21A to 21C illustrate a number of different configurations for directional electrodes for use with implantable stimulator devices described above. FIG. 21A illustrates directional electrodes 2102A to 2102C, each having a substantially rectangular shape with a width about two times their length. Structure 2104 is underneath the illustrated electrodes and may house receiving antennas, circuitry, or connector pads. FIG. 21B illustrates directional electrodes 2106A to 2106C, each with a rectangular shape as well. However, these electrodes 2106A to 2106C have lengths that are substantially longer than their widths (e.g., about 4-10 times as long). In other words, the rectangular electrodes may have a wide range of aspect ratios to cater towards the modulation needs of a particular application. Structure 2108 is underneath the illustrated electrodes and may house receiving antennas, circuitry, or connector pads. FIG. 21C illustrates yet another implementations of electrodes 2110A to 2110C. Electrodes 2110A and 2110C are shaped in a triangle while electrode 2110B is shaped in a trapezoid. Particularly, electrodes 2110A to 2110C are three electrodes that can be cut from a single rectangular metal sheet. Example material for the electrodes may include any biocompatible material such as MP35N, platinum, platinum/iridium or other biocompatible alloy. The surface area and contour of the electrodes may specifically tooled to adapt to the size and shape of the targeted excitable tissue. One skilled in the art will recognize that a variety of different electrode configurations may be used and the configuration options are not limited to those shown in FIGS. 21A-C.

A number of implementations have been described. Nevertheless, it will be understood that various modifications may be made. Accordingly, other implementations are within the scope of the following claims.

What is claimed is:

1. A method for modulating excitable tissue in a body of a patient comprising:
   placing a wireless implantable stimulator device at a target site in the patient's body, the wireless stimulator device including one or more electrodes each having a conducting surface and mounted on an inner surface of the wireless stimulator device such that the conducting surface of each electrode solely faces an inside of the stimulator device;
   reconfiguring the wireless implantable stimulator device such that the wireless implantable stimulator device reshapes at the target site from a first configuration incapable of forming an enclosure to substantially surround the excitable tissue to a second configuration that forms an enclosure that substantially surrounds the excitable tissue at the target site with the electrodes on the inside of the enclosure and the conducting surface of each electrode facing solely towards the excitable tissue; and
   wirelessly transmitting electrical energy from a pulse generator located outside the patient's body and through non-inductive coupling to the wireless implantable stimulator device such that (i) electrical impulses are generated solely using the electrical energy received non-inductively; (ii) the electrical impulses are delivered to the electrodes on the wireless implantable stimulator device; and (iii) neural modulation is applied from the conducting surface of each electrode to the excitable tissue substantially surrounded by the enclosure.

2. The method of claim 1, wherein placing the wireless implantable stimulator device comprises:
   placing an introducer into the patient's body near the target site;

constraining the wireless implantable stimulator device that is a helical wireless implantable stimulator device into a substantially linear shape within an inner lumen of the introducer; and advancing the helical wireless implantable stimulator device through the inner lumen of the introducer to the target site and out of a distal end of the inner lumen of the introducer towards the excitable tissue such that the helical wireless implantable stimulator device spirals around the excitable tissue to form the enclosure substantially surrounding the excitable tissue.

3. The method of claim 2, wherein the inner lumen of the introducer is 1.2 mm or less in diameter.

4. The method of claim 2, wherein constraining comprises:

inserting a stylet into a proximal end of the helical wireless implantable stimulator device.

5. The method of claim 1, wherein placing the wireless implantable stimulator device comprises:

surgically creating an opening on the patient's body;

through the opening, exposing the excitable tissue at a target site in the patient's body;

positioning the wireless implantable stimulator device that is an unfolded cylindrical implantable stimulator device adjacent to the exposed excitable tissue at the target site; and folding the foldable cylindrical implantable stimulator device around the excitable tissue to form the enclosure substantially surrounding the excitable tissue.

6. The method of claim 1 wherein placing the wireless implantable stimulator device comprises:

placing an introducer into the patient's body towards the target site; and advancing the wireless implantable stimulator device that is a foldable cylindrical wireless implantable stimulator device through an inner lumen of the introducer towards the target site until the foldable cylindrical wireless implantable stimulator device exits a distal end of the inner lumen of the introducer in an folded position;

unfolding the foldable cylindrical implantable stimulator device;

positioning the unfolded cylindrical implantable stimulator device adjacent to the excitable tissue at the target site; and folding the foldable cylindrical implantable stimulator device around the excitable tissue to form the enclosure substantially surrounding the excitable tissue.

7. The method of claim 6, wherein said unfolding comprises:

pivoting a portion of the foldable cylindrical wireless stimulator device about a hinge.

8. The method of claim 6, wherein said folding comprises:
pivoting a portion of the foldable cylindrical wireless stimulator device about a hinge.

9. The method of claim 1 wherein the electrodes of the wireless stimulator device include directional electrodes.

10. A device for modulating excitable tissue in a patient's body comprising:

a wireless implantable stimulator device that includes one or more electrodes on an inner surface of the wireless implantable stimulator device, each electrode having a conducting surface solely facing an inside of the stimulator device, the wireless implantable stimulator device being reconfigurable in-situ and inside the patient's body from a first configuration incapable of forming an enclosure to substantially surround the excitable tissue to a second configuration that forms an enclosure to substantially surround the excitable tissue and the conducting surface of each electrode faces solely towards the excitable tissue such that when electrical energy is transmitted wirelessly from a pulse generator located outside the patient's body and through non-inductive coupling to the wireless stimulator device, (i) electrical impulses are generated solely using the electrical energy received non-inductively; (ii) the electrical impulses are delivered to the electrodes on the wireless implantable stimulator device; and (iii) neural modulation is applied from the conducting surface of each electrode to the excitable tissue substantially surrounded by the enclosure.

11. The device of claim 10, wherein the first configuration includes a portion of the wireless implantable stimulator device shaped substantially linear and the second configuration includes the portion shaped substantially helical.

12. The device of claim 11, wherein the portion shaped substantially helical forms the enclosure that substantially surrounds the excitable tissue.

13. The device of claim 10, wherein the wireless implantable stimulator device comprises a cylindrical implantable stimulator device and wherein the first configuration is an open position of the cylindrical implantable stimulator device and the second configuration is a closed position of the cylindrical implantable stimulator device.

14. The device of claim 13, wherein the implantable stimulator device further comprises a hinge, a first portion and a second portion; and wherein the first portion and the second portion are coupled together with the hinge and are pivotable about the hinge to move from the open position to the closed position.

15. The device of claim 10, wherein the electrodes of the wireless implantable stimulator device include directional electrodes.

16. The device of claim 10, wherein the wireless implantable stimulator device further comprises a receiving antenna and circuitry, wherein the receiving antenna is configured to receive an input signal containing electrical energy and waveform parameters through electrical radiative coupling from a transmitter located outside of the patient's body and wherein the circuitry is configured to create one or more electrical impulses by harvesting the electrical energy from the input signal, the electrical impulse sufficient to modulate the excitable tissue substantially surrounded by the enclosure.

17. A system for modulating excitable tissue in a body of a patient, the system comprising:

a stimulator device comprising one or more electrodes and a receiving antenna, each electrode having a conducting surface solely facing an inside of the stimulator device, the wireless implantable stimulator device being reconfigurable in-situ and inside the patient's body from a first configuration incapable of forming an enclosure to substantially surround the excitable tissue to a second configuration that forms an enclosure to substantially surround the excitable tissue and the conducting surface of each electrode faces solely towards the excitable tissue such that when electrical energy is transmitted wirelessly from a pulse generator located outside the patient's body and through non-inductive coupling to the wireless stimulator device, (i) electrical impulses are generated solely using the electrical energy received non-inductively; (ii) the electrical impulses are delivered to the electrodes on the wireless implantable stimulator device; and (iii) neural modulation is applied from the conducting surface of each electrode to the excitable tissue substantially surrounded by the enclosure; and a control device having a transmitter located outside of the patient's body and configured to transmit an input signal containing electrical energy and waveform parameters to the receiving antenna through electrical radiative coupling, wherein the stimulator device is configured to generate one or more electrical impulses by harvesting the electrical energy from the input signal, the electrical impulses sufficient to modulate the excitable tissue.

18. The system of claim 17, wherein the control device comprises a transmitting antenna configured to transmit the input signal through a carrier signal having a frequency between about 800 KHz and 5.8 GHz.

19. The system of claim 17, wherein the control device comprises a pulse generator configured to generate electrical impulses with a frequency of about 10 to 500 Hz.

20. The system of claim 17 wherein the control device is configured to transmit the input signal to the targeted site tissue inside the patient's body within 12 cm of skin surface of the patient.

21. The system of claim 17, wherein the first position includes a portion of the wireless implantable stimulator device shaped substantially linear and the second position includes is the portion shaped substantially helical.

22. The system of claim 21, wherein the portion shaped substantially helical forms the enclosure that substantially surrounds the excitable tissue.

23. The system of claim 17, wherein the electrodes comprise directional electrodes and are positioned on the inner surface of the enclosure.

24. The system of claim 17, wherein the stimulator device comprises a cylindrical implantable stimulator device and wherein the first configuration is an open position of the cylindrical implantable stimulator device and the second configuration is a closed position of the cylindrical implantable stimulator device.

25. The system of claim 24, wherein the stimulator device further comprises a hinge, a first portion and a second portion; and wherein the first portion and the second portion are coupled together with the hinge and are pivotable about the hinge to move from the open position to the closed position.

* * * * *